(12) United States Patent
Jung et al.

(10) Patent No.: US 12,291,721 B2
(45) Date of Patent: May 6, 2025

(54) ACTIVATED LYMPHOCYTES COMPRISING CYTOKINE-INDUCED KILLER CELLS AND PREPARATION METHOD THEREFOR

(71) Applicant: GREENCROSSCELL, Seoul (KR)

(72) Inventors: Gyou Chul Jung, Yongin-si (KR); Dong Young Kim, Yongin-si (KR); Ji Min Lee, Yongin-si (KR)

(73) Assignee: GREENCROSSCELL, Seoul (KR)

( * ) Notice: Subject to any disclaimer, the term of this patent is extended or adjusted under 35 U.S.C. 154(b) by 852 days.

(21) Appl. No.: 17/434,814

(22) PCT Filed: May 4, 2020

(86) PCT No.: PCT/KR2020/005896
§ 371 (c)(1),
(2) Date: Aug. 30, 2021

(87) PCT Pub. No.: WO2020/231058
PCT Pub. Date: Nov. 19, 2020

(65) Prior Publication Data
US 2022/0160763 A1 May 26, 2022

(30) Foreign Application Priority Data

May 16, 2019 (KR) .................. 10-2019-0057531
Dec. 16, 2019 (KR) .................. 10-2019-0168127

(51) Int. Cl.
| | | |
|---|---|---|
| C12N 5/078 | (2010.01) | |
| A61K 40/10 | (2025.01) | |
| A61K 40/42 | (2025.01) | |
| A61P 35/00 | (2006.01) | |
| C12N 5/0783 | (2010.01) | |

(52) U.S. Cl.
CPC ............ *C12N 5/0634* (2013.01); *A61K 40/10* (2025.01); *A61K 40/42* (2025.01); *A61P 35/00* (2018.01); *C12N 5/0646* (2013.01); *A61K 2239/31* (2023.05); *A61K 2239/38* (2023.05); *A61K 2239/46* (2023.05); *C12N 2501/2302* (2013.01); *C12N 2501/515* (2013.01)

(58) Field of Classification Search
None
See application file for complete search history.

(56) References Cited

U.S. PATENT DOCUMENTS

2010/0233192 A1* 9/2010 Park .................. A61P 35/00
435/377

FOREIGN PATENT DOCUMENTS

| CN | 102112600 A | 6/2011 |
|---|---|---|
| CN | 106199005 A | 12/2016 |
| JP | 5097856 B2 | 12/2012 |
| KR | 10-2008-0018089 A | 2/2008 |
| KR | 10-2009-0127973 A | 12/2009 |
| KR | 10-2018-0032366 A | 3/2018 |
| KR | 10-2019-0004722 A | 1/2019 |

OTHER PUBLICATIONS

Kim HM, Lim J, Yoon YD, Ahn JM, Kang JS, Lee K, Park SK, Jeong YJ, Kim JM, Han G, Yang KH, Kim YJ, Kim Y, Han SB. Anti-tumor activity of ex vivo expanded cytokine-induced killer cells against human hepatocellular carcinoma. Int Immunopharmacol. Dec. 15, 2007;7(13):1793-801. (Year: 2007).*
Jabbarpour Z, Aghayan SS, Moradzadeh K, Ghaffari S, Ahmadbeigi N. The effect of serum origin on cytokines induced killer cell expansion and function. BMC Immunol. Sep. 1, 2023;24(1):28. (Year: 2023).*
Jia-Yan Wu et al., "The Critical Role of the NKG2D Receptor in CD8+CTL and CD8+CD56+ NKT Cell Cytotoxicity", Blood, 2004, vol. 104, No. 3164, 4pages.
Kenneth R. Meehan et al., "Adoptive Cellular Therapy using Cells Enriched for NKG2D⁺ CD3⁺ CD8⁺ T Cells after Autologous Transplantation for Myeloma", Biol Blood Marrow Transplant, 2013, vol. 19, pp. 129-137.
Cristina Maccalli et al., "TNK cells (NKG2D$^+$ CD8$^+$ or CD4$^+$ T lymphocytes) in the control of human tumors", Cancer Immunol Immunother, 2009, vol. 58, pp. 801-808.
Kenneth R Meehan et al., "Immune Mobilization with IL-2 and Growth Factors: Differential in Vivo Effects of the NKG2D Receptor on CD8+ and CD56+ Effector Cells", Blood, 2008, vol. 116, No. 3491, 4pages.
Laleh Talebian et al., "NKG2D, An NK Cell Activating Receptor on CD8 T Cells, Plays An Essential Role In Killing Myeloma Cells", Blood, 2010, vol. 116, No. 2087, 4pages.
Jianhua Liu et al., "Phenotypic characterization and anticancer capacity of CD8+ cytokine-induced killer cells after antigen-induced expansion", PLOS One, 2017, vol. 12, No. 4, 17pages.
Elisa Cappuzzello et al., "Cytokines for the induction of antitumor effectors: The paradigm of Cytokine-Induced Killer (CIK) cells", Cytokine & Growth Factor Reviews, 2017, vol. 36, pp. 99-105.
Jingting Jiang et al., "Cytokine-induced killer cells promote antitumor immunity", Journal of Translational Medicine, 2013, vol. 11, No. 83. 9pages.
Peter M. Anderson et al., "Augmentation of cell number and LAK activity in peripheral blood mononuclear cells activated with anti-CD3 and interleukin-2", Cancer Immunol Immunother, 1988, vol. 27, pp. 82-88.

(Continued)

*Primary Examiner* — Allison M Fox
*Assistant Examiner* — Alyssa G Weston
(74) *Attorney, Agent, or Firm* — Sughrue Mion, PLLC

(57) ABSTRACT

The present invention relates to activated lymphocytes comprising cytokine-induced killer cells in which CD8$^+$CD56$^+$NKG2D$^+$ cells are present at a proportion of 20% or more, and a preparation method therefor, and more particularly, to activated lymphocytes comprising cytokine-induced killing cells which have high tumor cell killing abilities and growth rates and are almost free of side effects because they do not require the combined administration of interleukin-2, and a preparation method therefor.

1 Claim, 11 Drawing Sheets

(56) References Cited

OTHER PUBLICATIONS

International Searching Authority, International Search Report for PCT/KR2020/005896 dated Aug. 10, 2020 [PCT/ISA/210].
Office Action issued Dec. 5, 2023 in Chinese Application No. 202080017747.1.
Office Action issued May 23, 2024 in Chinese Application No. 202080017747.1.

* cited by examiner

ACTIVATED LYMPHOCYTES COMPRISING CYTOKINE-INDUCED KILLER CELLS AND PREPARATION METHOD THEREFOR

CROSS REFERENCE TO RELATED APPLICATIONS

This application is a National Stage of International Application No. PCT/KR2020/005896 filed May 4, 2020, claiming priority based on Korean Patent Application No. 10-2019-0057531 filed May 16, 2019 and Korean Patent Application No. 10-2019-0168127 filed Dec. 16, 2019.

TECHNICAL FIELD

The present invention relates to activated lymphocytes including cytokine-induced killer cells, and a preparation method therefor.

BACKGROUND ART

Cancer is caused by accumulation of various genetic variations and loss of normal cellular regulatory processes. In a process of regulating the incidence of cancer, the immune system should go through several sequential processes in order to effectively kill cancer cells. This is called "a cancer immunity cycle". In a first process of the cancer immune cycle as a first step, a new tumor antigen (neoantigen) generated by tumorigenesis is released and dendritic cells (DC) act to treat the same. In this process, elements such as pro-inflammatory cytokines are released from dying tumor cells. In a second step, the antigens captured by dendritic cells are labeled in the form of MHC-I and MHC-II molecules, which activate effector T cells so as to react to tumor-specific antigens. In a final step, activated effector T cells move and infiltrate to a tumor location, thereby specifically recognizing tumor cells and causing apoptosis thereof. However, the above cancer immune cycle does not work normally in patients suffering from cancer.

With regard to a role of the immune system in suppression and promotion of cancer incidence, there is "Cancer Immunoediting" and this is generally divided into three (3) steps. A first step is "Elimination", which refers to a cancer immune-surveillance process to detect an occurrence of tumors and kill the same together with activation of innate immunity and acquired (adaptive) immunity. This process is substantially the same as that of the cancer immunity cycle ("CIC") described above. Further, a second step is "Equilibrium", a process in which the tumor survived in the elimination step, and the acquired immunity prevents the tumor from proliferation while immunogenicity is formed in the tumor. In this process, the immune system maintains so-called "functional dormant state" for residual tumor cells, which is considered to be the longest time-consuming step in the cancer immune editing process. Finally, a third step is "Escape" in which tumor cells avoid the immune system and are proliferated. At this step, tumor cells lose antigen but have increased resistance to cytotoxic immunity. Further, tumor microenvironments are in immunosuppressive state, and immunosuppressive cytokines such as VEGF, TGF-beta, etc. are secreted from the tumor. In addition, regulatory T cells secrete interleukin-10 and TGF-beta to inhibit the function of tumor-specific T lymphocytes, express negative co-stimulatory molecules (such as PD-1), and consume interleukin-2, thus inducing a deterioration in functions of CTL.

As the method for treating cancer, surgery, which is the longest used method from before the 1890s to the present, since then, radiation therapy, chemotherapy and precision medical therapy have been developed. In the case of treating cancer by a surgical method, there is a disadvantage that tumor may not be completely removed because a surgical range may be limited. When treating the cancer with radiation therapy and chemotherapy, not only cancer cells but also normal cells are affected by toxicity, thus to often accompany strong side effects. In the case of precision medical therapy, the optimal treatment method is provided by comprehensively analyzing different genomic information, environmental factors, and lifestyle for each patient. However, the standard treatment method currently applied in the art uses a method deduced from the results of a specific group, therefore, there is a disadvantage that this method cannot treat all diseases of diverse individuals genetically and biochemically. Anticancer immunotherapy is a method of inducing, strengthening or suppressing the immune system in cancer patients to treat the cancer, which is classified into active immunotherapy and passive immunotherapy. The active immunotherapy has advantages that therapeutic effects are maintained for a long period of time although the response is slow. Representative active immunotherapy includes vaccines and immune checkpoint inhibitors. The passive immunotherapy is characterized by a fast response but a short duration. Representative passive immunotherapy methods include tumor infiltrating lymphocyte (TIL), monoclonal antibody, chimeric antigen receptor (CAR) T cell and acquired immunotherapy.

The acquired immunotherapy is a method of inducing differentiation and proliferation through a culture process that can enhance anticancer activity in vitro after collecting blood from the patient and separating only immune cells, and injecting the activated immune cells back into the patient, thus to improve anticancer effect. Lymphokine-activated killer (LAK) cells with increased cytotoxic activity were obtained by culturing monocytes isolated from the peripheral blood of cancer patients in the presence of interleukin-2, and then, were used to attempt treatment of the cancer patients. Tumor infiltration lymphocytes (TIL) present in cancer tissues of the cancer patients were isolated and cultured in the same manner and used for treatment of the cancer patients.

However, since these existing immunotherapy methods use high concentrations of interleukin-2, side effects occurred due to the same, and it was difficult to secure the sufficient number of lymphocytes to induce therapeutic effects.

Accordingly, the present inventors have developed an anticancer immunocytotherapeutic agent composition that does not have serious side effects because it has superior tumor cell killing ability and high proliferation rate compared to LAK cells and does not require combined administration of interleukin-2, and therefore, the present invention has been completed on the basis of the above development.

SUMMARY OF INVENTION

Problems to be Solved by Invention

An object of the present invention is to provide activated lymphocytes including cytokine-induced killer cells having high tumor cell killing ability and proliferation rate.

In addition, another object of the present invention is to provide activated lymphocytes including cytokine-induced killer cells with very little side effects.

Further, another object of the present invention is to provide activated lymphocytes including the above activated lymphocytes.

Means for Solving Problems

To achieve the above objects, the following technical solutions are adopted in the present invention.
1. Activated lymphocytes including CD8+CD56+NKG2D+ cells.
2. The activated lymphocytes according to the above 1, wherein a ratio of the CD8+CD56+NKG2D+ cells is 20% or more.
3. The activated lymphocytes according to the above 1, wherein a ratio of the CD8+CD56+NKG2D+ cells is 20% to 30%.
4. An anticancer immunocytotherapeutic agent composition including the activated lymphocytes according to any one of the above 1 to 3.
5. The composition according to the above 4, wherein the cancer is at least one selected from the group consisting of: pancreatic cancer, gastric cancer, breast cancer, malignant lung neoplasm, ovarian cancer, brain neoplasm, bile duct cancer, colorectal cancer, gallbladder cancer, rectal cancer, malignant melanoma, cervical cancer, cholangiocarcinoma, colon cancer, metastatic gastric cancer, glioblastoma, kidney cancer, duodenal neoplasm, salivary gland neoplasm, esophageal cancer, endometrial cancer, sinus cancer, small intestinal carcinoma, Ewing's sarcoma, uterine sarcoma, malignant neoplasm of Barter's bulge, prostate cancer, prostate neoplasm, osteosarcoma, glioblastoma polymorph, astrocytoma, uterine cancer, thymoma, endocrine neoplasm, soft tissue cancer, brain stem gliomas, recurrent ovarian cancer, tongue neoplasm, liposarcoma, neurofibroma, neuroendocrine carcinoma, bladder cancer, malignant neoplasm, lymphoma, skin nerve endocrine carcinoma, adrenal cancer, rhabdomyosarcoma, neoplasm, uterine leiomyoma, metastatic breast cancer, liver cancer, colorectal cancer and signet ring cell carcinoma.
6. The composition according to the above 4, wherein the cancer is at least one selected from the group consisting of liver cancer, kidney cancer, pancreatic cancer, malignant melanoma, prostate cancer and colorectal cancer.
7. A method for preparation of activated lymphocytes including CD8+CD56+NKG2D+ cells, the method including; culturing lymphocytes isolated from peripheral blood in a medium containing anti-CD3 antibody, interleukin-2 and fetal bovine serum (FBS).
8. The method according to the above 7, wherein sorting the cells is not included.
9. The method according to the above 7, wherein the culture is conducted in two or more steps, wherein a medium in a first step includes anti-CD3 antibody, interleukin-2 and FBS, and a medium in a second step includes interleukin-2 and FBS.
10. The method according to the above 7, wherein the medium does not contain IFN-γ (interferon-gamma), while contain 20% or more of CD8+CD56+NKG2D+ cells.
11. The method according to the above 7, wherein a concentration of the anti-CD3 antibody is 1 to 10 μg/ml, a concentration of interleukin-2 of the medium in the first and second steps is 100 to 800 U/ml, and a concentration of FBS is 0.1 to 15% by volume.
12. The method according to the above 7, wherein the culture is conducted in three steps, wherein a medium in a first step contains anti-CD3 antibody, interleukin-2 and FBS, while a medium in a second step and a third step contains interleukin-2 and FBS but does not contain anti-CD3 antibody, and wherein a concentration of the anti-CD3 antibody is 1 to 10 μg/ml, a concentration of interleukin-2 of the medium in each of the first, second and third steps is 100 to 800 U/ml, and a concentration of FBS of the medium in the first step is 5 to 15% by volume, a concentration of FBS of the medium in the second step is 0.1 to 1% by volume, and a concentration of FBS of the medium in the third step is 0.1 to 2% by volume.
13. A pharmaceutical composition for prevention or treatment of cancer, including the activated lymphocytes according to any one of the above 1 to 3.
14. The composition according to the above 13, wherein the cancer is at least one selected from the group consisting of: pancreatic cancer, gastric cancer, breast cancer, malignant lung neoplasm, ovarian cancer, brain neoplasm, bile duct cancer, colorectal cancer, gallbladder cancer, rectal cancer, malignant melanoma, cervical cancer, cholangiocarcinoma, colon cancer, metastatic gastric cancer, glioblastoma, kidney cancer, duodenal neoplasm, salivary gland neoplasm, esophageal cancer, endometrial cancer, sinus cancer, small intestinal carcinoma, Ewing's sarcoma, uterine sarcoma, malignant neoplasm of Barter's bulge, prostate cancer, prostate neoplasm, osteosarcoma, glioblastoma polymorph, astrocytoma, uterine cancer, thymoma, endocrine neoplasm, soft tissue cancer, brain stem gliomas, recurrent ovarian cancer, tongue neoplasm, liposarcoma, neurofibroma, neuroendocrine carcinoma, bladder cancer, malignant neoplasm, lymphoma, skin nerve endocrine carcinoma, adrenal cancer, rhabdomyosarcoma, neoplasm, uterine leiomyoma, metastatic breast cancer, liver cancer, colorectal cancer and signet ring cell carcinoma.
15. The composition according to the above 13, wherein the cancer is at least one selected from the group consisting of liver cancer, kidney cancer, pancreatic cancer, malignant melanoma, prostate cancer and colorectal cancer.
16. The composition according to the above 13, wherein the composition includes the activated lymphocytes, saline and human serum albumin.

Advantageous Effects

The activated lymphocytes of the present invention may include CD8+CD56+NKG2D+ cells to exhibit excellent anticancer activity.

The activated lymphocytes of the present invention may have a very high ratio of CD8+CD56+NKG2D+ cells to maximize the anticancer activity.

The preparing method of the present invention may produce activated lymphocytes including CD8+CD56+NKG2D+ cells.

MODE FOR CARRYING OUT INVENTION

Figure 1:
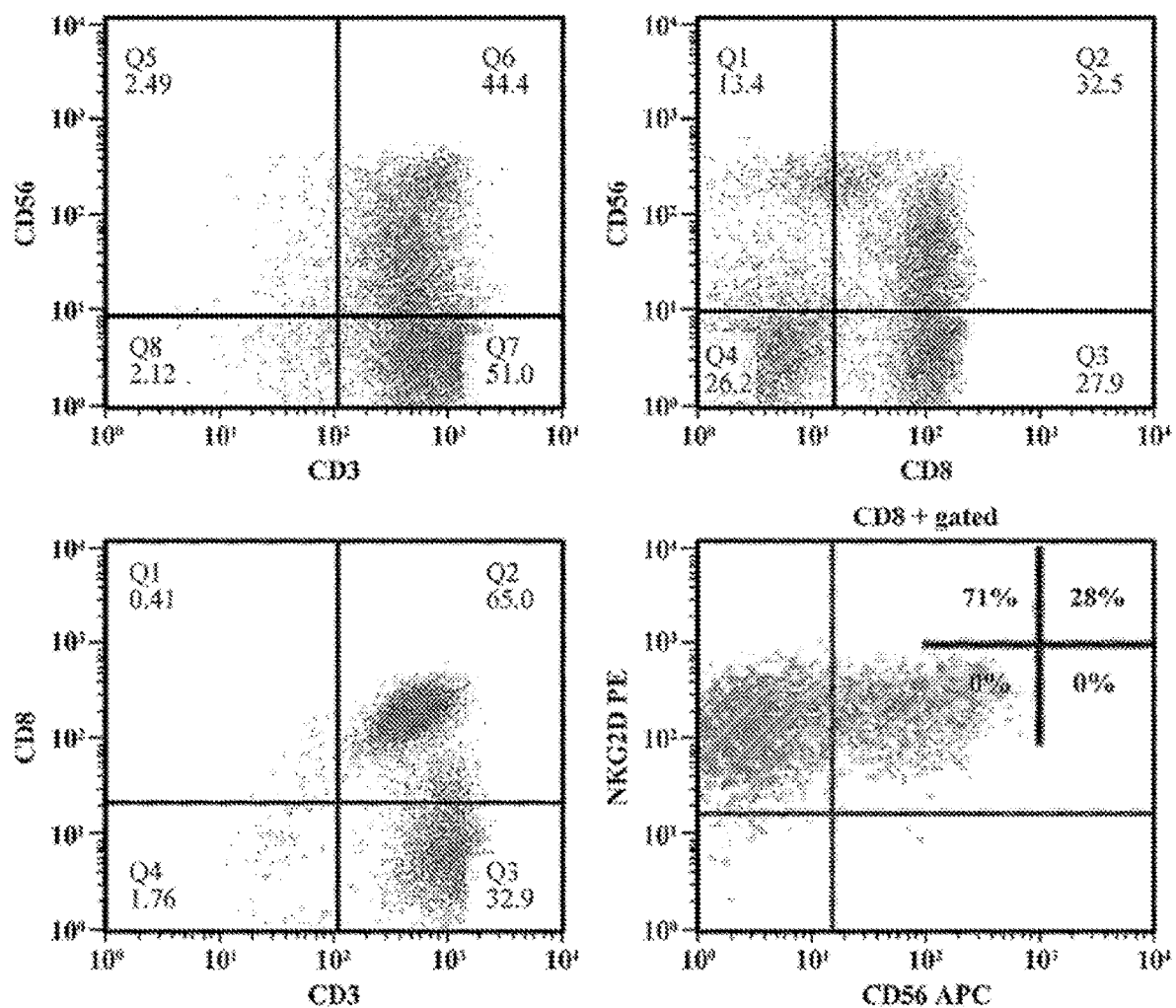
FIG. 1 is images illustrating cell phenotype in activated lymphocytes confirmed using FACS assay.
Figure 2:
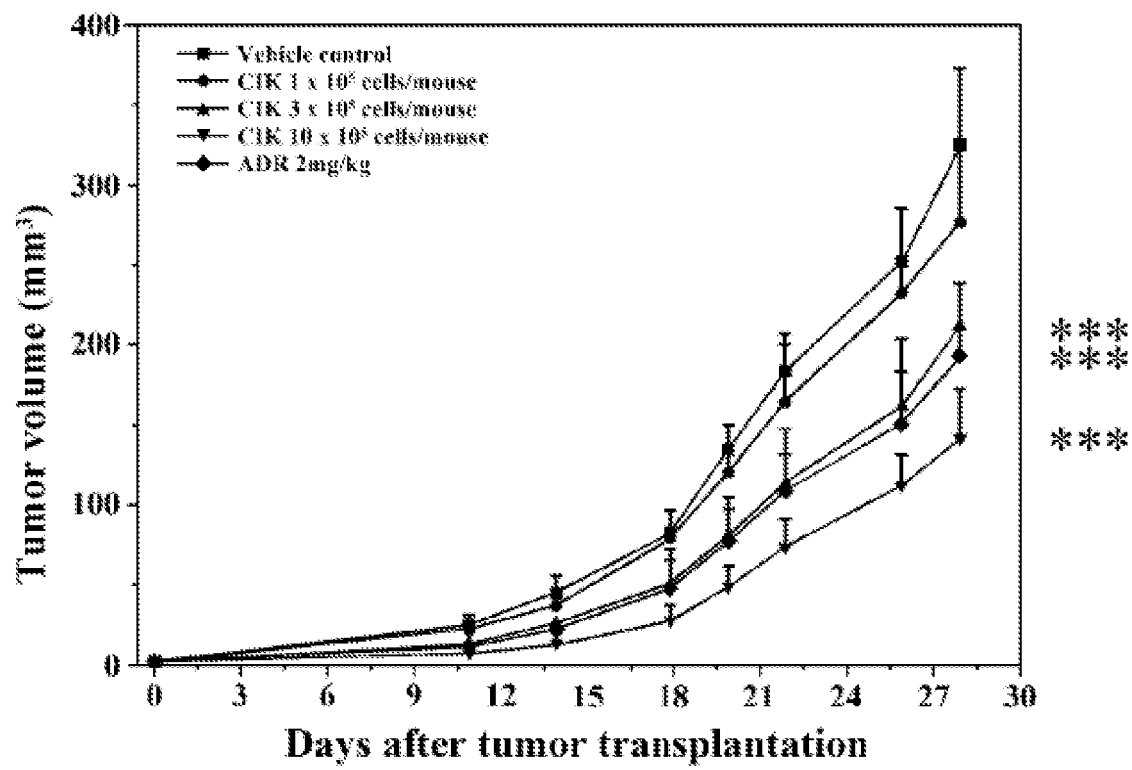
FIG. 2 is graphs illustrating results of investigation of anticancer effects of activated lymphocytes on human renal cancer (ACHN).
Figure 2:
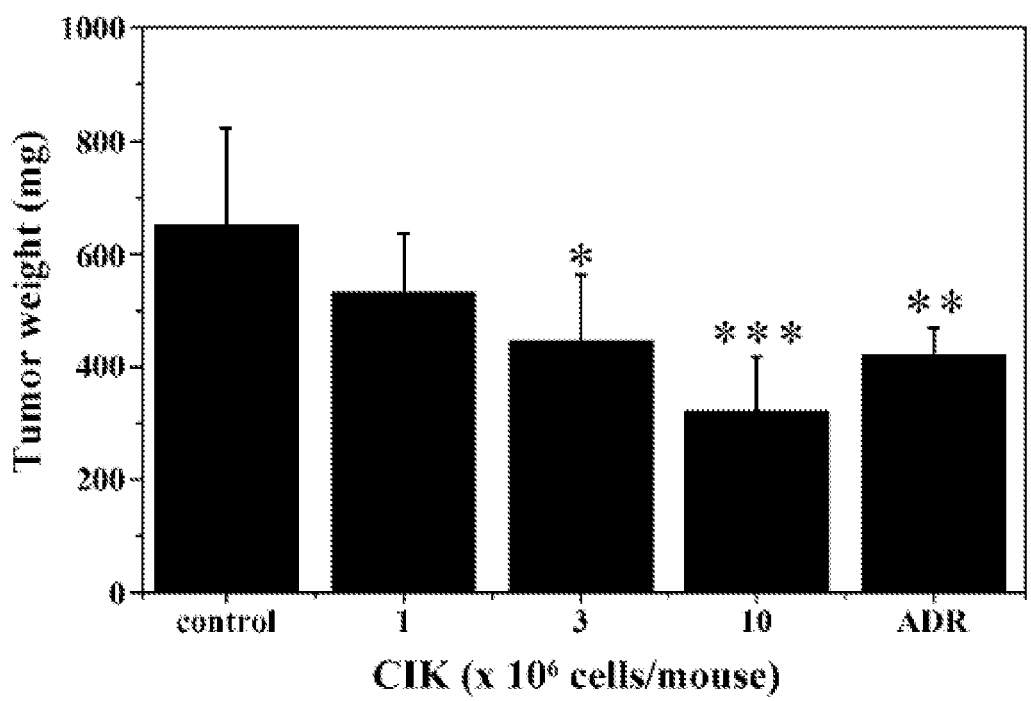
Figure 3:
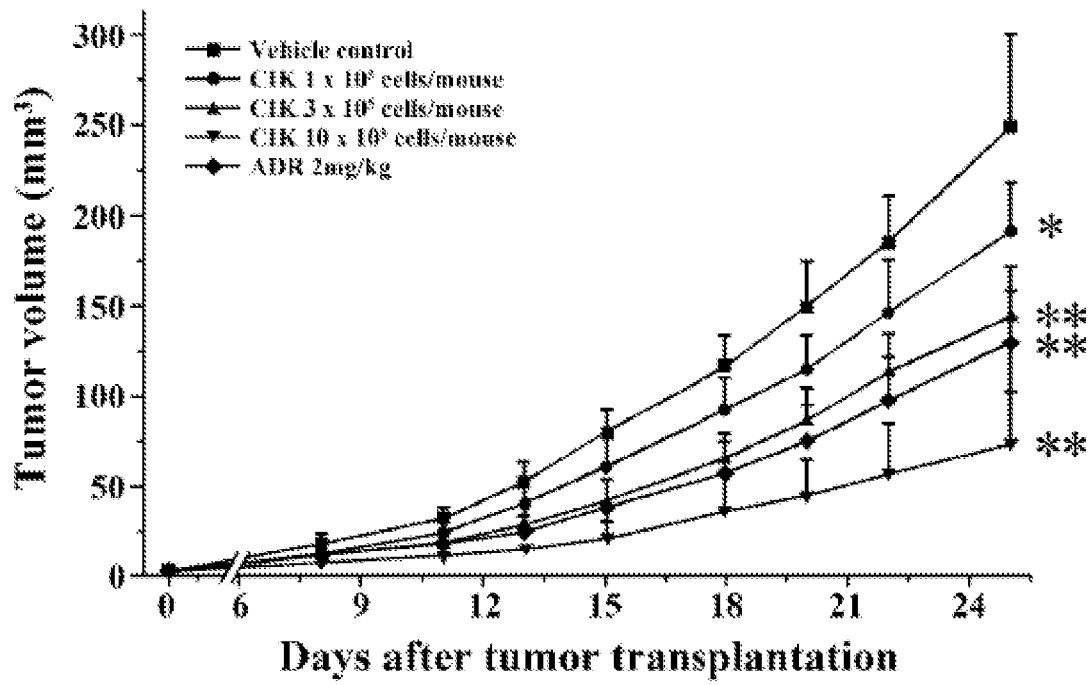
FIG. 3 is graphs illustrating results of investigation of anticancer effects of activated lymphocytes on human pancreatic cancer (AsPC-1).
Figure 3:
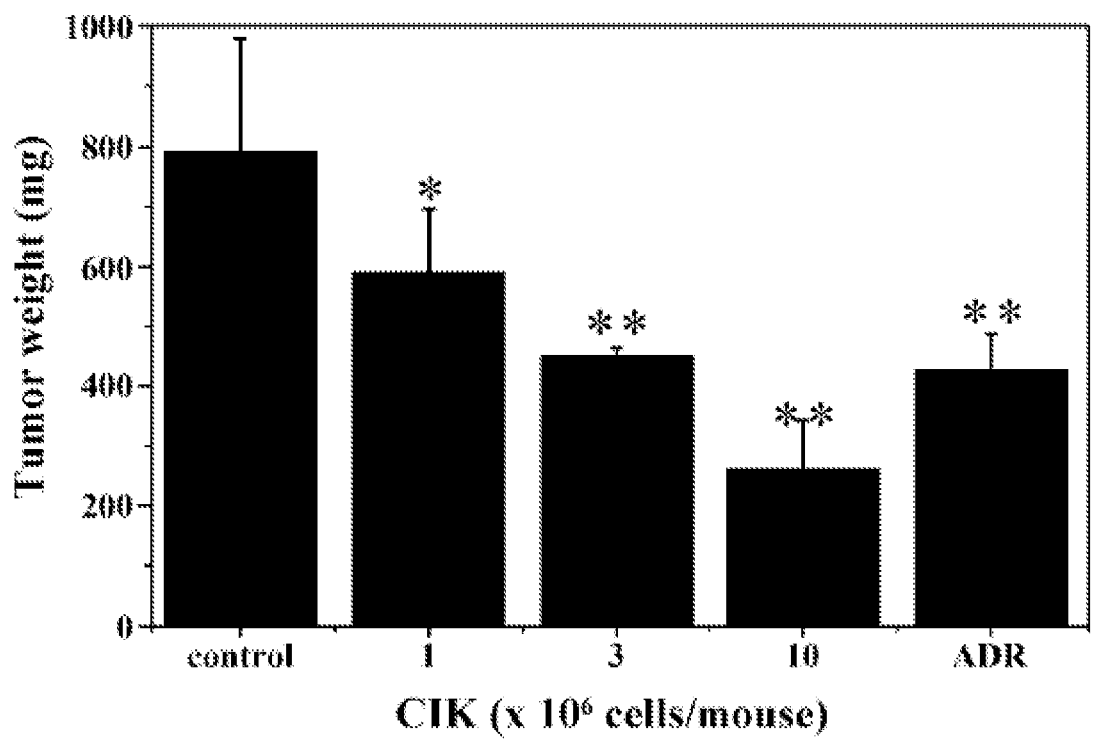
Figure 4:
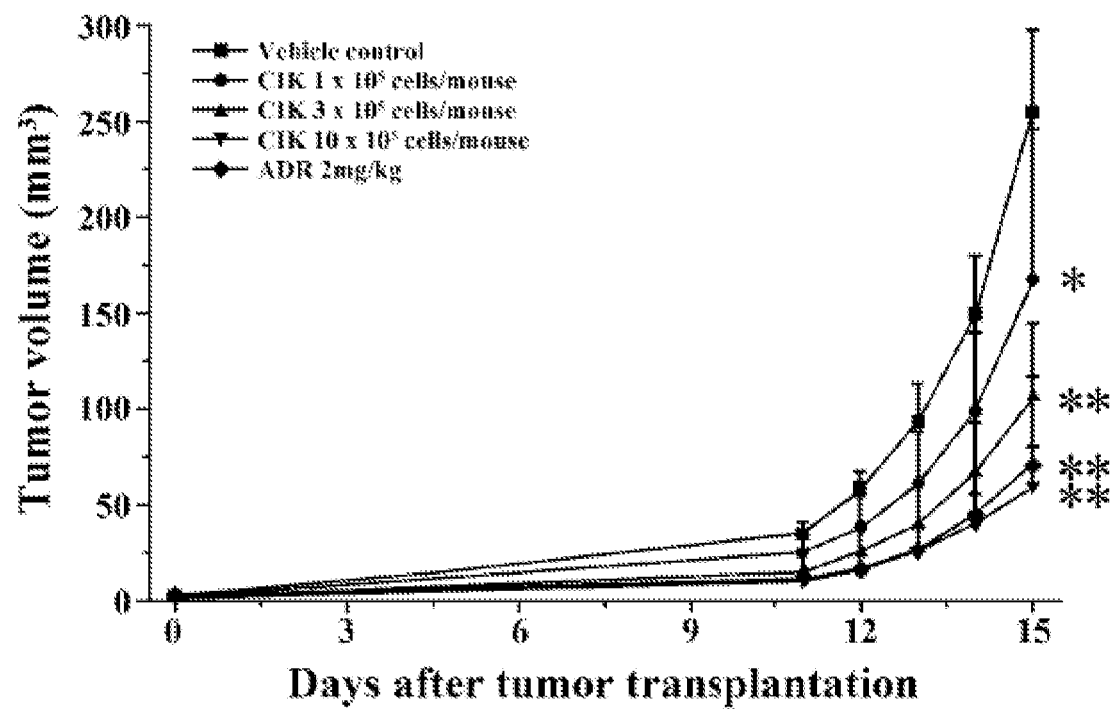
FIG. 4 is graphs illustrating results of investigation of anticancer effects of activated lymphocytes on human melanoma cancer (LOX-IMV1).
Figure 4:
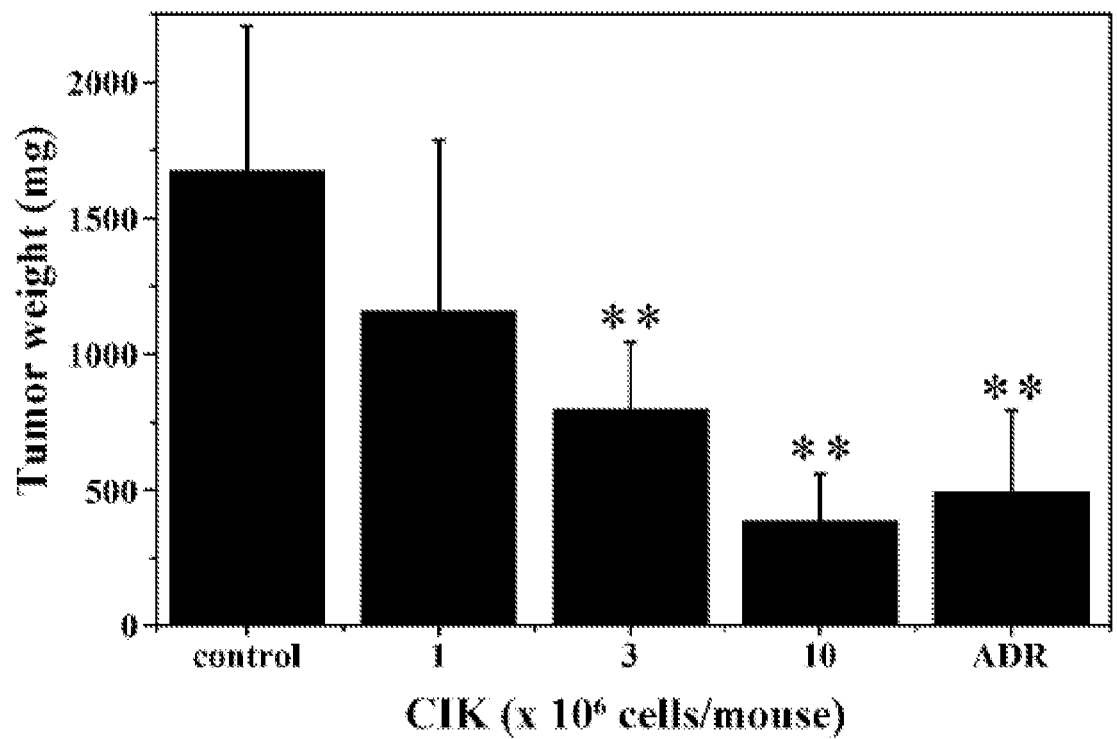
Figure 5:
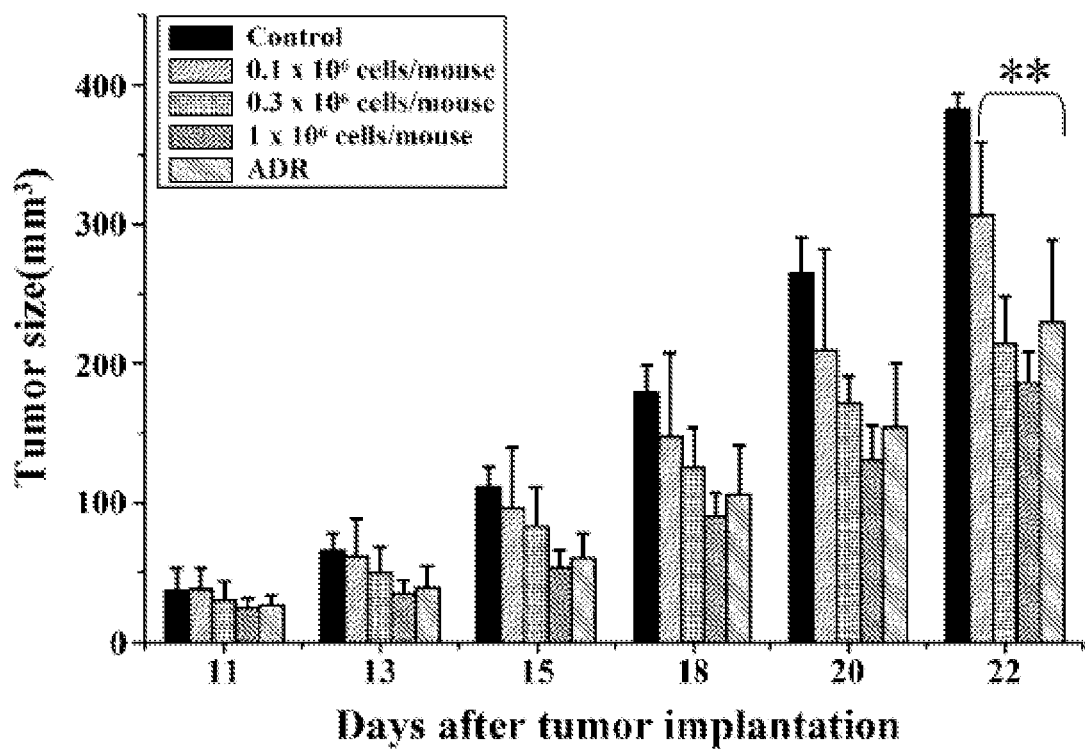
FIG. 5 is graphs illustrating results of investigation of anticancer effects of activated lymphocytes on human prostate cancer (PC-3).
Figure 5:
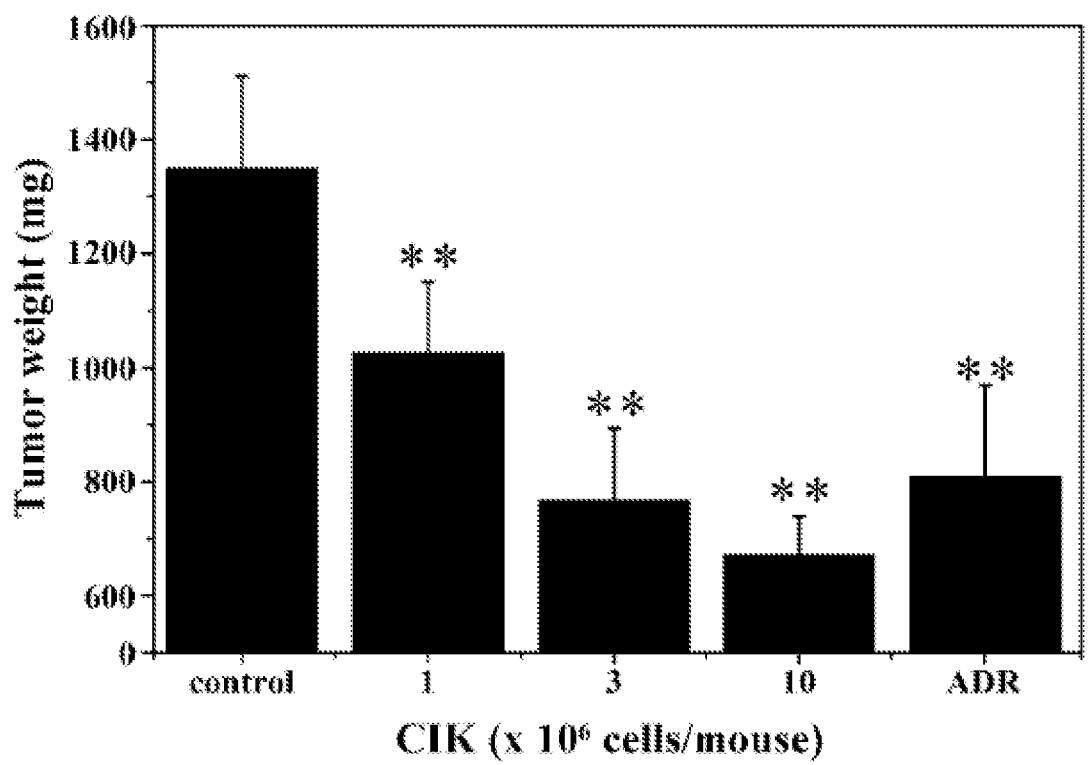
Figure 6:
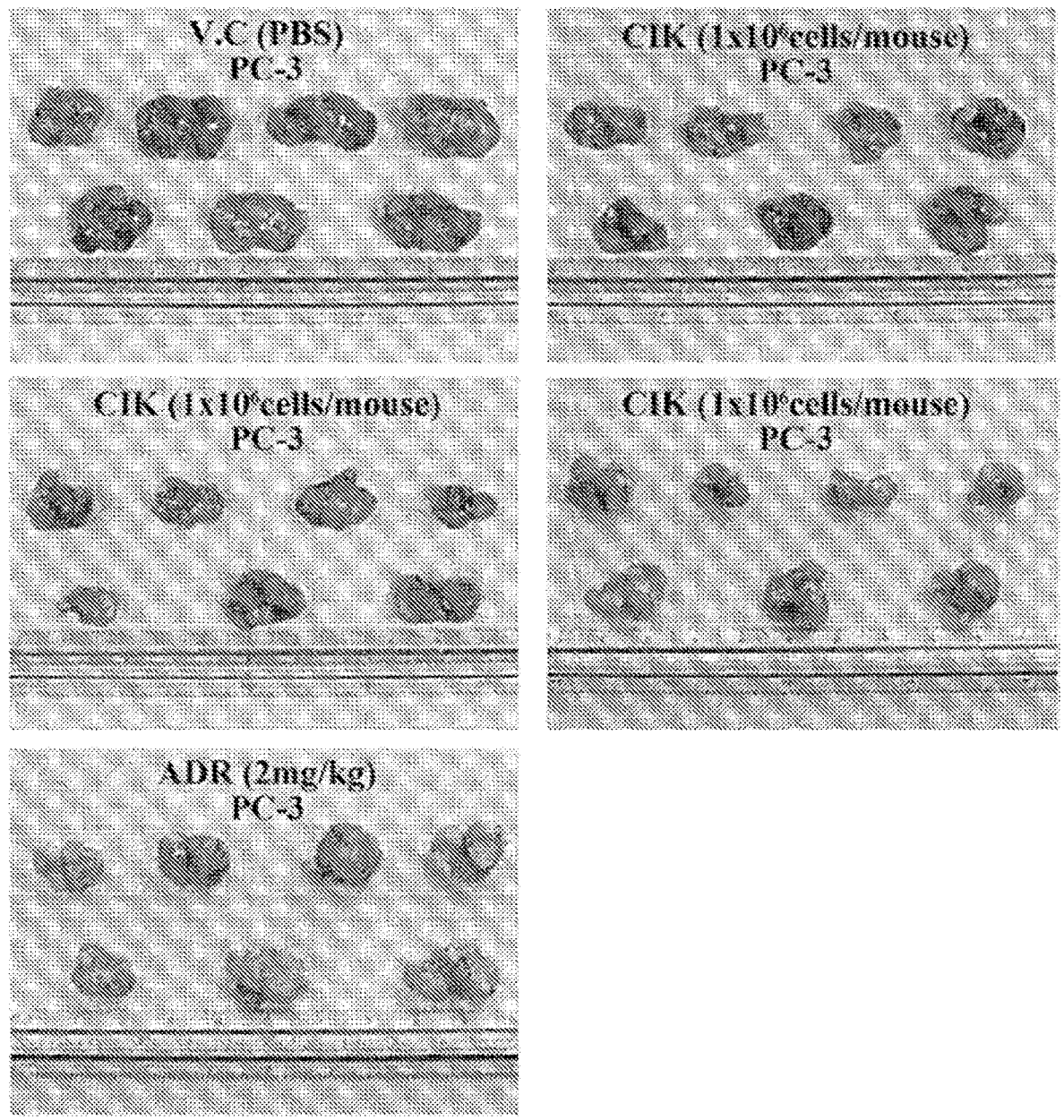
FIG. 6 is images illustrating results of investigation of anticancer effects of activated lymphocytes on human prostate cancer (PC-3).
Figure 7:
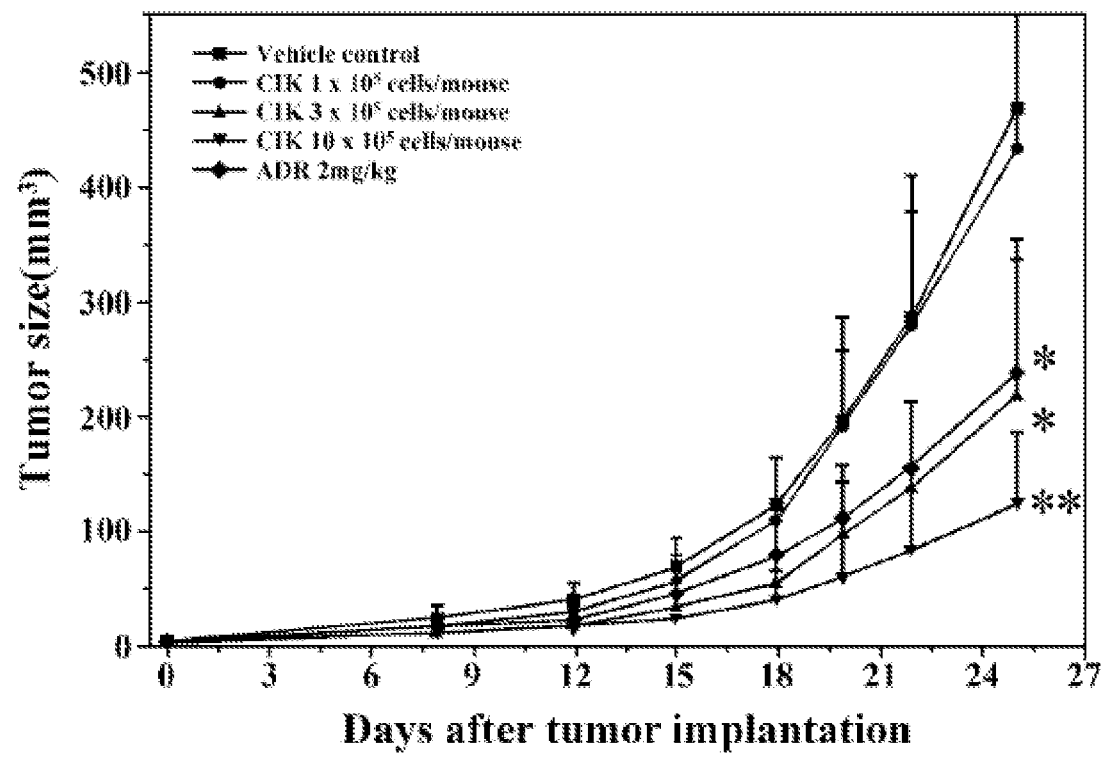
FIG. 7 is graphs illustrating results of investigation of anticancer effects of activated lymphocytes on human colon cancer (SW620).
Figure 7:
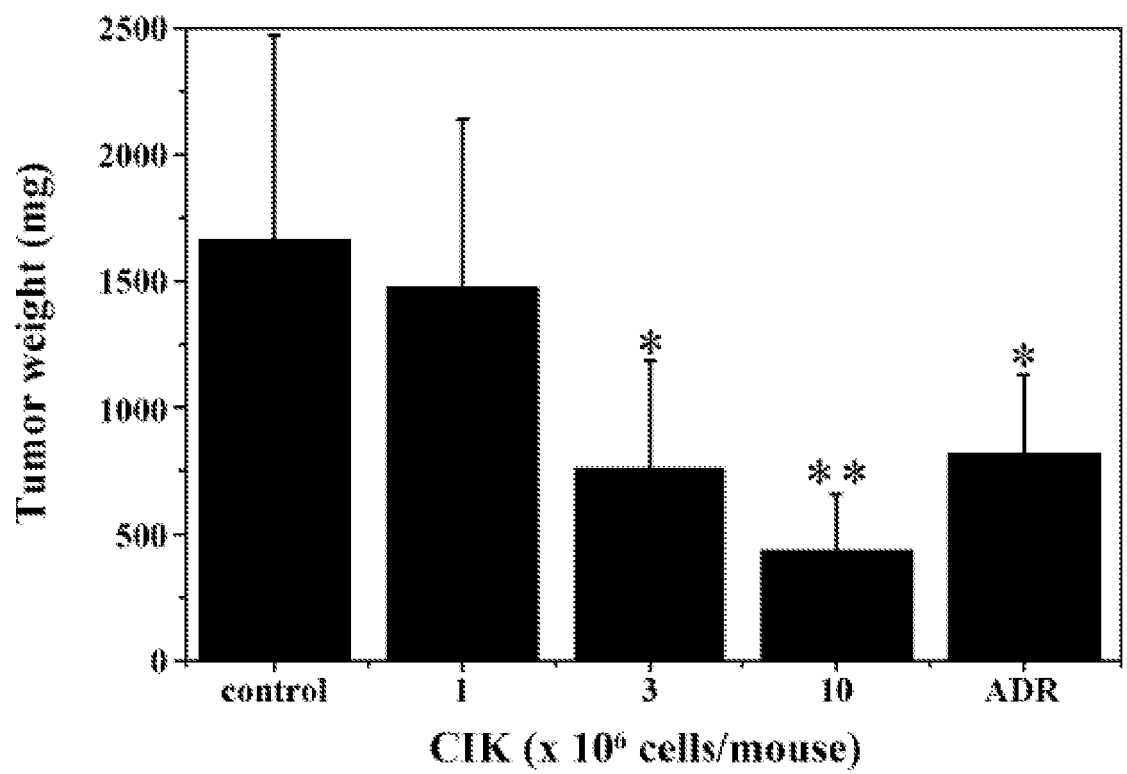
Figure 8:
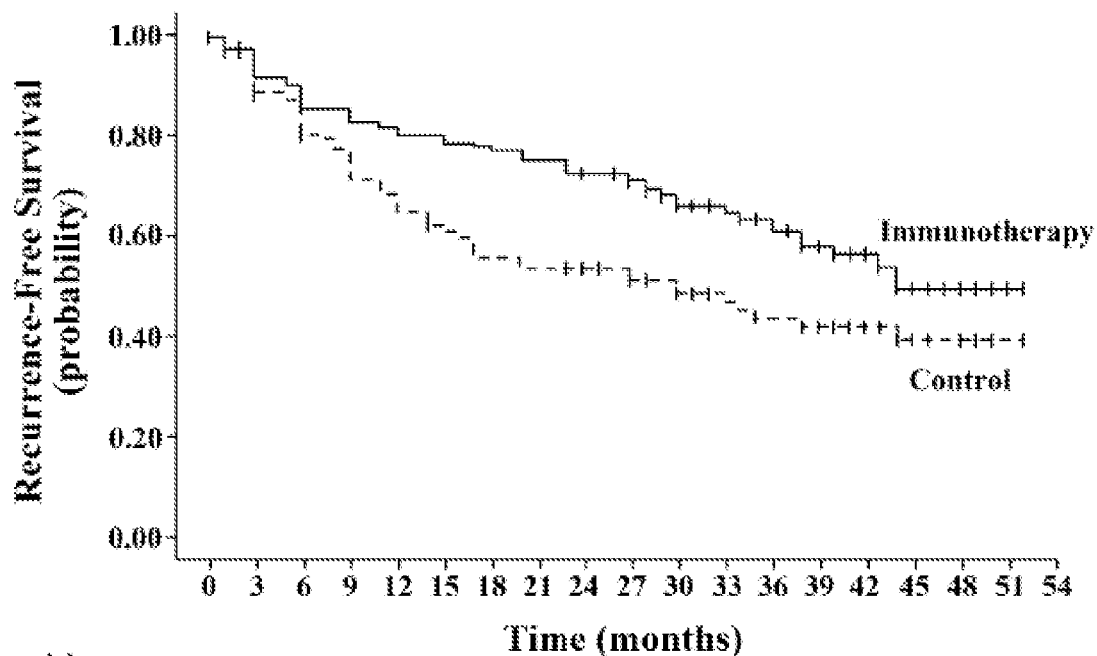
FIG. 8 is graphs illustrating results of clinical trial for activated lymphocytes to liver cancer.
Figure 8:
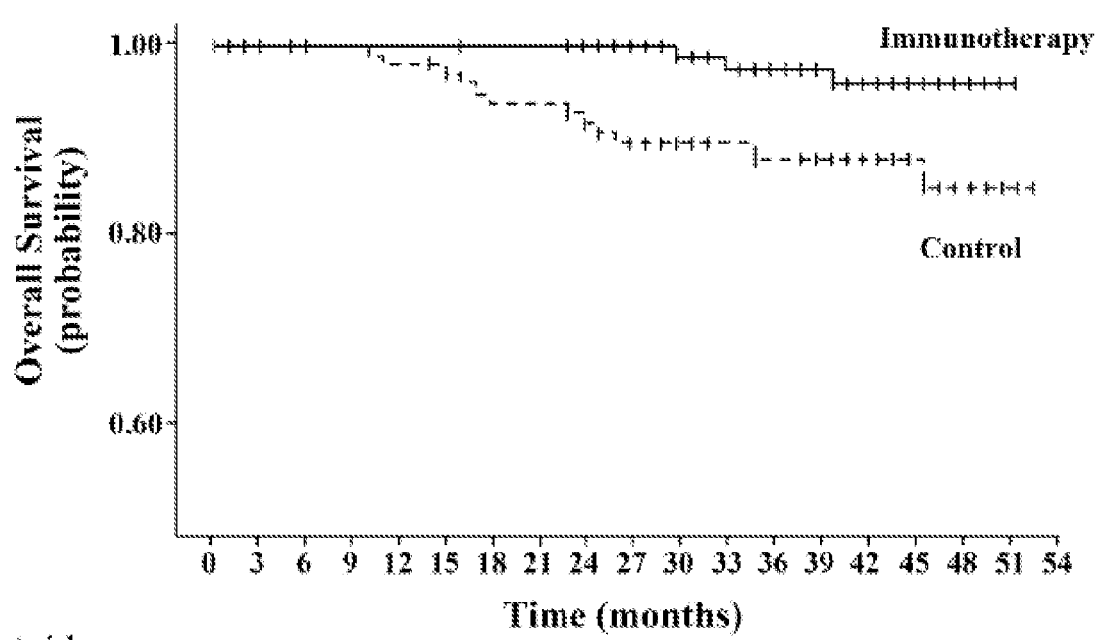
Figure 9:
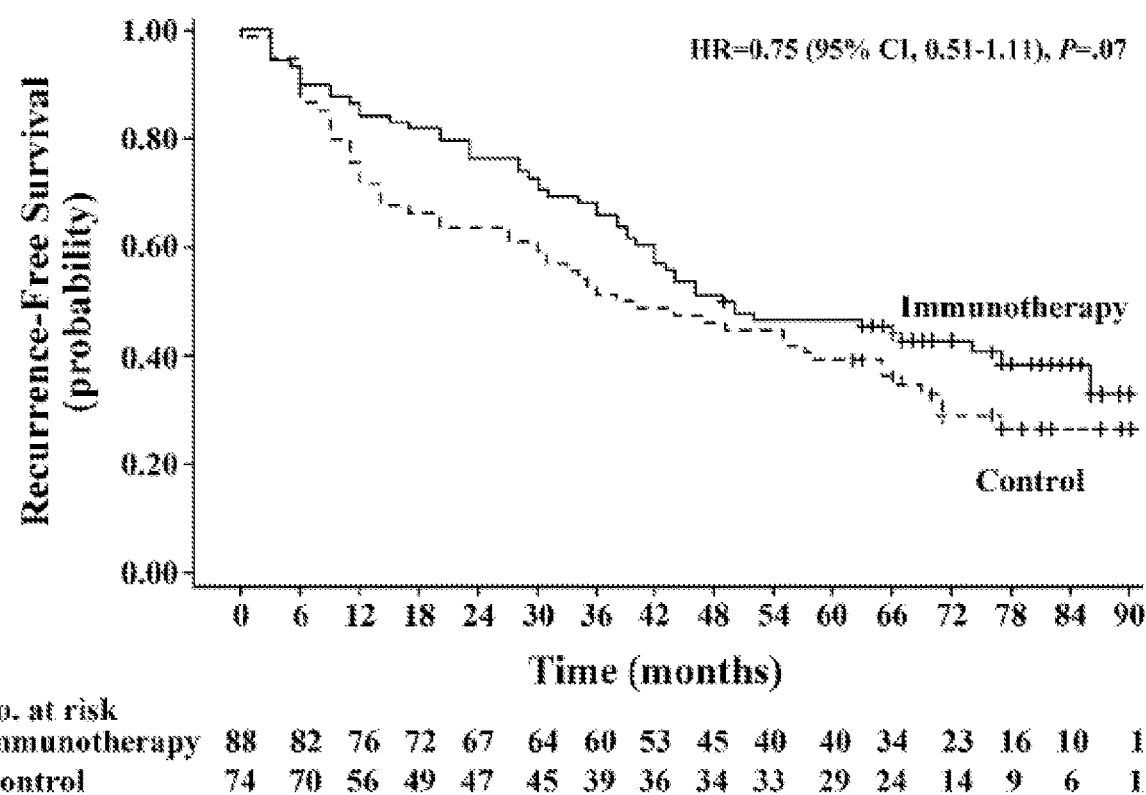
FIG. 9 is a graph illustrating results of long-term follow-up of clinical trial for activated lymphocytes to liver cancer.
Figure 10:
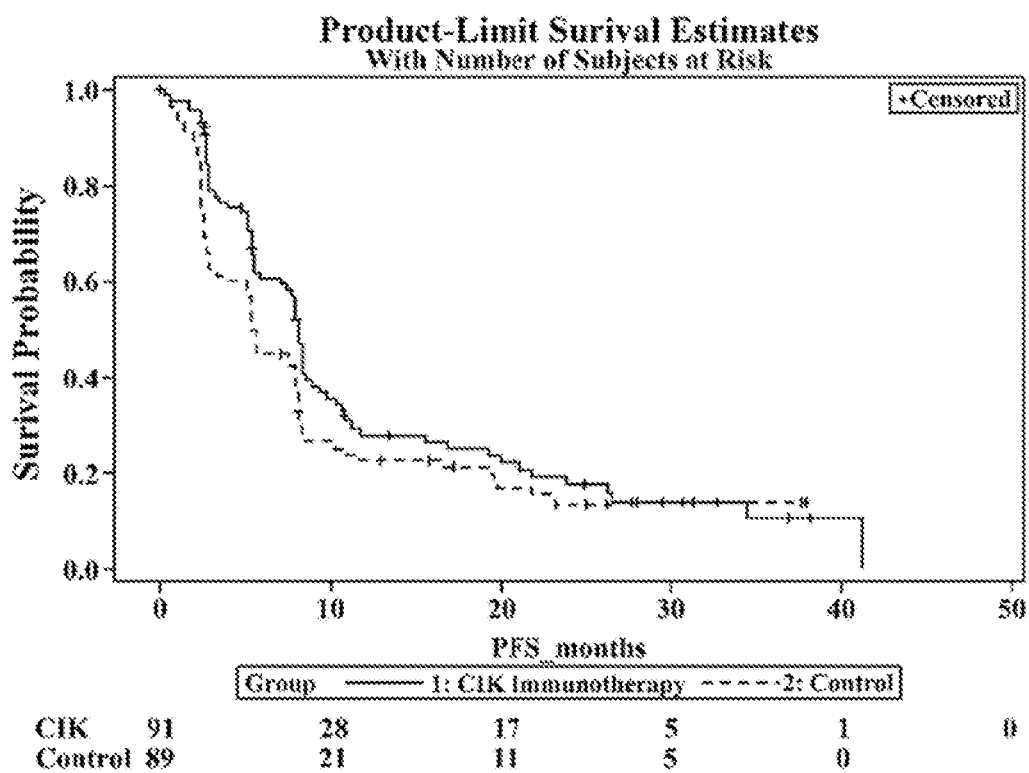
FIG. 10 is graphs illustrating results of clinical trial for activated lymphocytes to glioblastoma.
Figure 10:
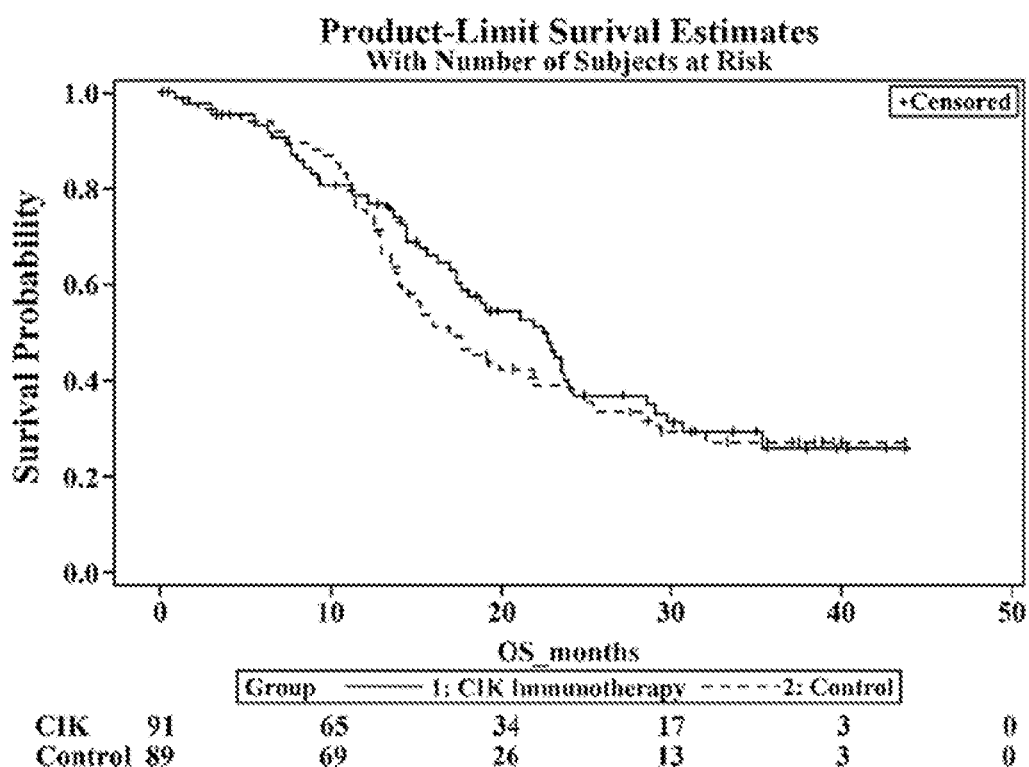
Figure 11:
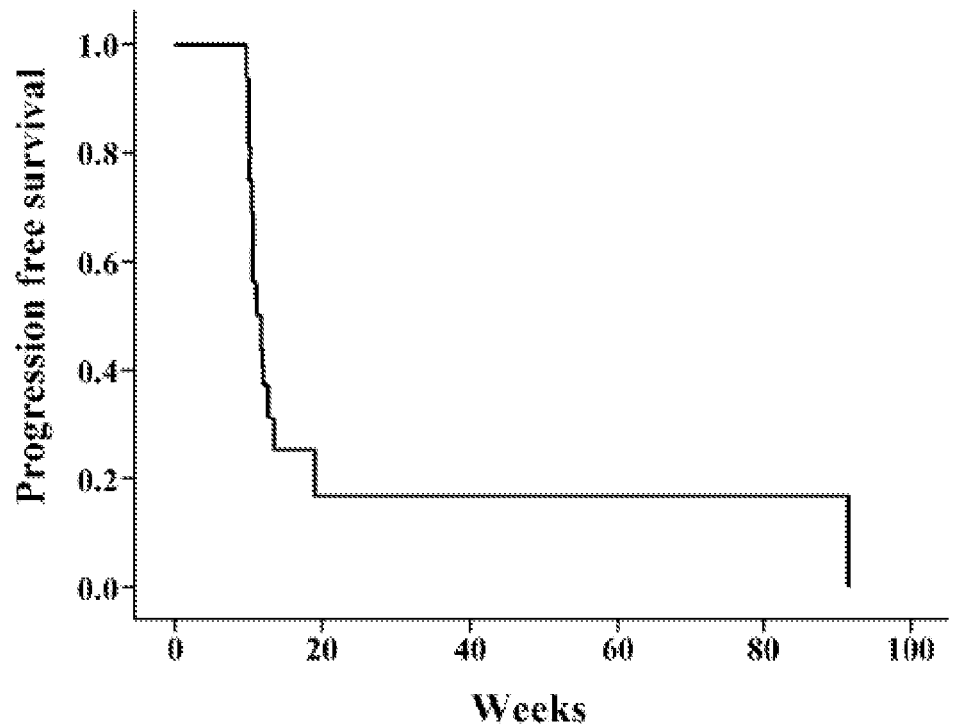
FIG. 11 is graphs illustrating results of clinical trial for activated lymphocytes to pancreatic cancer.
Figure 11:
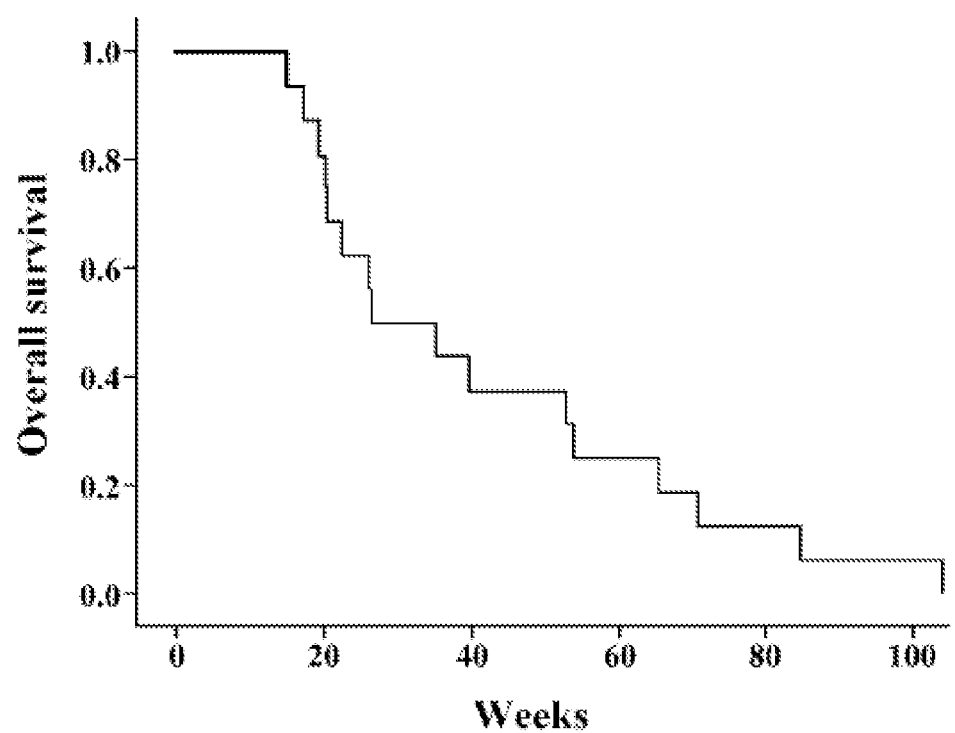

Hereinafter, the present invention will be described in detail.

The present invention relates to activated lymphocytes.

The activated lymphocytes as used herein are a population of immune effector cells, in particular, are a heterogeneous cell population including $CD3^+CD56^+$ cells, $CD8^+CD56^+$ cells, $CD3^+CD8^+$ cells and the like.

The activated lymphocytes of the present invention may include $CD8^+CD56^+NKG2D^+$ cells.

When including the $CD8^+CD56^+NKG2D^+$ cells, it is possible to exhibit excellent anticancer efficacy.

A proportion of $CD8^+CD56^+NKG2D^+$ cells may be, for example, 20% or more, specifically 20 to 30%, and more specifically 25 to 30%, but it is not limited thereto. When including the $CD8^+CD56^+NKG2D^+$ cells in a large amount, it is possible to maximize anticancer efficacy.

The activated lymphocytes of the present invention may include cells having several phenotypes, for example, $CD3^+CD56^+$, $CD8^+CD56^+$, $CD3^+CD8^+$, and like.

In particular, in the activated lymphocytes of the present invention, a proportion of $CD3^+CD56^+$ cells may be, for example, 40% or more, specifically 40 to 60%, and more specifically 40% to 50%, but it is not limited thereto.

The proportion of $CD8^+CD56^+$ cells may be, for example, 30% or more, specifically 30 to 40%, and more specifically 30% to 35%, but it is not limited thereto.

The proportion of $CD3^+CD8^+$ cells may be, for example, 60% or more, specifically 60 to 90%, and more specifically 60% to 70%, but it is not limited thereto.

The activated lymphocytes of the present invention may be obtained by activating, proliferating and culturing lymphocytes isolated from peripheral blood, specifically, the activated lymphocytes may be obtained by culturing lymphocytes isolated from peripheral blood in a medium containing anti-CD3 antibody, interleukin-2 and FBS, but it is not limited thereto.

Further, the present invention relates to an anticancer immunocytotherapeutic agent composition including the above-described activated lymphocytes.

In the present invention, the immunocytotherapeutic agent is one of the anticancer immunocytotherapeutic agents to treat cancer by massively proliferating and activating immune cells present in blood of a person in vitro, and then, administrating the activated immune cells back to the person, which is a personalized anticancer therapeutic agent that activates the patient's own immune cells to induce in vivo immunity, like the anticancer immunocytotherapeutic agents using dendritic cells.

The composition of the present invention may include the above-described activated lymphocytes, thus to exhibit excellent anticancer effects.

The cancers to be prevented or treated by the composition of the present invention may include, for example, pancreatic cancer, gastric cancer, breast cancer, malignant lung neoplasm, ovarian cancer, brain neoplasm, bile duct cancer, colorectal cancer, gallbladder cancer, rectal cancer, malignant melanoma, cervical cancer, cholangiocarcinoma, colon cancer, metastatic gastric cancer, glioblastoma, kidney cancer, duodenal neoplasm, salivary gland neoplasm, esophageal cancer, endometrial cancer, sinus cancer, small intestinal carcinoma, Ewing's sarcoma, uterine sarcoma, malignant neoplasm of Barter's bulge, prostate cancer, prostate neoplasm, osteosarcoma, glioblastoma polymorph, astrocytoma, uterine cancer, thymoma, endocrine neoplasm, soft tissue cancer, brain stem gliomas, recurrent ovarian cancer, tongue neoplasm, liposarcoma, neurofibroma, neuroendocrine carcinoma, bladder cancer, malignant neoplasm, lymphoma, skin nerve endocrine carcinoma, adrenal cancer, rhabdomyosarcoma, neoplasm, uterine leiomyoma, metastatic breast cancer, liver cancer, colorectal cancer, signet ring cell carcinoma, and the like, but it is not limited thereto The composition of the present invention may be formulated and used in the forms of oral dosage such as powders, granules, tablets, capsules, suspensions, emulsions, syrups and aerosols; external preparations; suppositories; and sterile injectable solutions according to conventional methods.

Carriers, excipients and diluents possibly contained in the composition of the present invention may include, for example, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil. When formulating the composition, the formulation may be prepared using diluents or excipients such as fillers, extenders, binders, wetting agents, disintegrants, and surfactants that are usually used in the art. Solid preparations for oral administration may include tablets, pills, powders, granules, capsules, etc., and such solid preparations may be produced by mixing the above-described compound with at least one excipient such as starch, calcium carbonate, sucrose or lactose, gelatin, etc. Further, in addition to simple excipients, lubricants such as magnesium stearate and talc may also be used. Liquid preparations for oral administration may include suspensions, liquid solutions, emulsions, syrups, etc. In addition to water and liquid paraffin, which are commonly used as simple diluents, a variety of excipients such as wetting agents, sweetening agents, fragrances, and preservatives may also be included. Meanwhile, preparations for parenteral administration may include sterile aqueous solutions, non-aqueous solvents, suspensions, emulsions, lyophilized preparations, and suppositories. As the non-aqueous solvent and suspension, propylene glycol, polyethylene glycol, vegetable oil such as olive oil, and injectable ester such as ethyl oleate may be used. As a base for suppositories, witepsol, macrogol, tween 61, cacao butter, laurin, glycerogelatin, and the like may be used.

An amount of the composition of the present invention may vary depending on the age, sex and weight of the patient. However, for example, a composition containing $1\times10^9$ to $2\times10^{10}$ cells may be administered, and a dose thereof may be, for example, 100 to 1,000 ml, and specifically 100 to 300 ml. In addition, the dose may be increased or decreased depending on a route of administration, a degree of disease, sex, weight, age of the patient and the like. Therefore, the dose does not limit the scope of the present invention in any way.

Further, the present invention relates to a method for preparing activated lymphocytes including $CD8^+CD56^+$ $NKG2D^+$ cells.

The method of the present invention may include culturing lymphocytes isolated from peripheral blood in a medium containing anti-CD3 antibody, interleukin-2 and FBS.

The peripheral blood may be autologous peripheral blood.

If necessary, the peripheral blood is centrifuged to remove an upper plasma layer and lymphocytes may be obtained from the separated monocyte layer.

The lymphocytes may be cultured in a medium containing anti-CD3 antibody, interleukin-2 and FBS, thereby activating and proliferating the lymphocytes.

A concentration of the anti-CD3 antibody is not particularly limited and may be, for example, 0.1 to 100 μg/ml, and specifically 1 to 10 μg/ml.

The anti-CD3 antibody may be applied to a culture flask and provided, but it is not limited thereto.

The concentration of interleukin-2 is not particularly limited and may be, for example, 50 to 1000 U/ml, and specifically 100 to 800 U/ml. Within the above range, 100 to 800 U/ml, 400 to 800 U/ml, 100 to 500 U/ml, 100 to 300 U/ml, etc. may be variously included.

The concentration of FBS is not particularly limited and may be, for example, 0.1 to 15% by volume ("vol. %").

The medium of the present invention may not contain interferon gamma (IFN-γ).

The medium according to the present invention may further include components commonly used for lymphocyte culture, T cell activation, colony proliferation, and long-term culture. For example, the medium may include glycine, L-arginine, L-asparagine. L-aspartic acid, L-cysteine 2HCl, L-glutamic acid, L-glutamine, L-histidine, L-hydroxyproline, L-isoleucine, L-leucine, L-lysine hydrochloride. L-methionine, L-phenylalanine, L-proline, L-serine, L-threonine. L-tryptophan. L-tyrosine disodium salt dihydrate, L-valine, biotin, choline chloride, D-calcium pantothenate, folic acid, niacinamide, para-aminobenzoic acid, pyridoxine hydrochloride, riboflavin, thiamine hydrochloride, vitamin B12, i-inositol, calcium nitrate, magnesium sulfate, potassium chloride, sodium bicarbonate, sodium chloride, sodium phosphate dibasic anhydrous, D-glucose, glutathione, HEPES, phenol red, and the like, but it is not limited thereto.

An example of commercially available products may be GIBCO's RPMI 1640 Medium, but it is not limited thereto.

If necessary, the culture may be performed in several steps. For example, the culture may be performed in one step or two or more steps.

When performing the culture in two or more steps, for example, lymphocytes cultured in step 1 may be separated and cultured in step 2 by transferring them to a new medium.

When performing the culture in two or more steps, the first step medium may contain an anti-CD3 antibody, interleukin-2 and FBS, while the second step medium may contain interleukin-2 and FBS. More specifically, the first step medium may contain an anti-CD3 antibody and interleukin-2, while the second step medium may contain interleukin-2 and FBS, but may not contain an anti-CD3 antibody.

The anti-CD3 antibody and interleukin-2, respectively, may be contained at a concentration within the above-described range, and the medium exemplified above may be used.

When performing the culture in two or more steps, the first step medium may contain 5 to 15 vol. % of FBS, and specifically 8 to 12 vol. % of FBS, while the second step medium may contain 0.1 to 2 vol. % of FBS, and specifically 0.3 to 1.5 vol. % of FBS, but it is not limited thereto.

When performing the culture in three steps, a medium in step 1 may contain 5 to 15 vol. % of FBS, and specifically 8 to 12 vol. % of FBS, a medium in step 2 may contain 0.1 to 1 vol. % of FBS, and specifically 0.3 to 0.8 vol. % of FBS, and a medium in step 3 may contain 0.1 to 2 vol. % of FBS, and specifically 0.5 to 1.5 vol. % of FBS, but it is not limited thereto.

The culture may be conducted in a general cell culture method, for example, in a $CO_2$ incubator. The CO 2 concentration may be, for example, 1 to 10%, and specifically 3 to 7%, and the temperature may be 30 to 40° C., and specifically 35 to 38° C., but it is not limited thereto.

The culture may be conducted until the lymphocytes are sufficiently activated and proliferated, and may be conducted, for example, for 10 to 30 days, and specifically for 12 to 21 days, but it is not limited thereto.

In order to improve culture efficiency, it is preferable to add a medium according to an increase in the number of cells during culture. The medium may be added, for example, in a cycle of once every 1 to 10 days, and specifically 1 to 7 days, so as to prevent a deterioration of the culture medium, but it is not limited thereto.

Then, if necessary, the medium may be centrifuged to remove the supernatant thus to separate the activated lymphocytes.

The culture period and an amount of the medium exemplified above may be appropriately adjusted according to a rate of increase and a degree of increase of the cells. Specifically, because a rate of cell growth depends on the donor of the cells, the culture period may be appropriately determined within the above range. Further, the medium may be further added or cells may be transferred to a large amount of medium.

In the method of the present invention, lymphocytes may be isolated from peripheral blood and frozen.

Specifically, the lymphocytes may be isolated from peripheral blood and frozen after culture. The culture may be conducted in the above-described medium.

Frozen lymphocytes may be thawed, and then cultured again to obtain activated lymphocytes.

The thawing may be conducted by heating the lymphocytes at 30 to 40° C. for 1 minute to 20 minutes, but it is not limited thereto.

The thawed lymphocytes may be cultured in a medium containing anti-CD3 antibody, interleukin-2 and FBS.

The concentrations of the anti-CD3 antibody, interleukin-2 and FBS may be within the above-described range, and the components described above may be used as the medium component, but it is not limited thereto Specifically, the culture of the thawed lymphocytes may be conducted in a single step or divided into two or more steps, and more specifically, the culture may be performed in three or more steps.

When performing the culture in two steps, for example, after a first culture in a medium containing no anti-CD3 antibody, a second culture in a medium containing the anti-CD3 antibody may be executed.

The first culture may be conducted, for example, for 1 to 3 days, and the second culture may be conducted, for example, for 2 to 5 days, but it is not limited thereto.

A concentration of the anti-CD3 antibody may be within the above-described range.

The medium of the third culture may not contain an anti-CD3 antibody.

In the third culture medium, FBS may be contained in an amount of, for example, 0.1 to 2 vol. %, and specifically 0.5 to 1.5 vol. %, but it is not limited thereto.

The method of the present invention may include the steps exemplified above, whereby activated lymphocytes with a high CD8'CD56'NKG2D' cell ratio may be obtained even without a separate cell sorting process (e.g., fluorescence activated cell sorting (FACS), magnetic activated cell sorting (MACS), etc.) to sort CD3%, CD8', CD56$^+$ or NKG2D$^+$ cells, collect only these cells, or selectively separate and culture these cells.

Further, the present invention relates to a pharmaceutical composition for preventing or treating cancer, which includes the activated lymphocytes.

The type of cancer is not particularly limited and may be at least one selected from the group consisting of, for example, pancreatic cancer, gastric cancer, breast cancer, malignant lung neoplasm, ovarian cancer, brain neoplasm, bile duct cancer, colorectal cancer, gallbladder cancer, rectal cancer, malignant melanoma, cervical cancer, cholangiocarcinoma, colon cancer, metastatic gastric cancer, glioblastoma, kidney cancer, duodenal neoplasm, salivary gland neoplasm, esophageal cancer, endometrial cancer, sinus cancer, small intestinal carcinoma, Ewing's sarcoma, uterine sarcoma, malignant neoplasm of Barter's bulge, prostate cancer, prostate neoplasm, osteosarcoma, glioblastoma polymorph, astrocytoma, uterine cancer, thymoma, endocrine neoplasm, soft tissue cancer, brain stem gliomas, recurrent ovarian cancer, tongue neoplasm, liposarcoma, neurofibroma, neuroendocrine carcinoma, bladder cancer, malignant neoplasm, lymphoma, skin nerve endocrine carcinoma, adrenal cancer, rhabdomyosarcoma, neoplasm, uterine leiomyoma, metastatic breast cancer, liver cancer, colon cancer and signet ring cell carcinoma. Specifically, the cancer described herein may be at least one selected from the group consisting of liver cancer, kidney cancer, pancreatic cancer, malignant melanoma, prostate cancer and colorectal cancer, but it is not limited thereto.

The composition may contain various carriers, excipients, diluents, and the like, as exemplified above. According to one embodiment, saline may be included, specifically, activated lymphocytes, saline and human serum albumin may be included, and more specifically, the composition may consist of only the above components.

Human serum albumin may be provided in a state of being included in saline, specifically 0.5% to 3%, and more specifically 1% human serum albumin may be used, but it is not limited thereto.

Hereinafter, the present invention will be described in detail and illustrated by means of the following examples.

EXAMPLE

Preparation of Activated Lymphocytes
1. Preparing Method 1
(1) Blood Sampling and Separation of Lymphocytes The activated lymphocytes used in the present invention may begin production by collecting 20-70 mL of autologous peripheral blood from a patient. The collected blood was transferred to a 250 mL test tube and diluted by 3 times with RPMI1640 in a ratio of 1:2, followed by dispensing 30-40 mL of diluted blood into a 50 mL test tube including Ficoll-paque dispensed therein without mixing the layers together, and centrifuging the tube at a rotational speed of 2.000 rpm and at room temperature for 20 minutes.

After removing the upper plasma layer slowly to prevent the cells of the lymphocyte layer from being sucked in, the separated monocyte layer was transferred to a 50 mL test tube. The separated monocyte layer was diluted by 3 times with RPM11640 in a ratio of 1:2, centrifuged at room temperature for 5 minutes at a rotational speed of 2,000 rpm, and then the supernatant was removed while releasing the collected cells.

(2) Lymphocyte Culture 1

The lymphocytes isolated in the above (1) were released in 50 mL of lymphhomedium, and 1 µg/ml to 10 µg/ml of anti-CD3 antibody was dispensed into a flask with a coated floor area of 225 cm$^2$, followed by beginning culture in a cell incubator at 37° C. and 5% $CO_2$. At this time, in the lymphomedium, interleukin-2 of 500 to 800 U/ml and 10% of FBS are contained. Lymphomedium further contains components commonly used in floating cell culture such as various mammalian cells including human leukemic cells, that is, the lymphomedium may be a medium containing, for example, calcium nitrate ($Ca(NO_3)_2$ $4H_2O$, 90 to 100 mg/L), potassium chloride (KCl, 380 to 400 mg/L), magnesium sulfate ($MgSO_4$, 40 to 50 mg/L), sodium chloride (NaCl, 5500 to 6000 mg/L), disodium hydrogen phosphate ($Na_2HPO_4$, 750 to 800 mg/L), D-glucose (1900 to 2000 mg/L), glutathione (0.8 to 1.5 mg/L), phenol red (4 to 6 mg/L), L-arginine (190 to 200 mg/L), L-asparagine (40 to 50 mg/L), L-aspartic acid (15 to 25 mg/L), L-cysteine 2 hydrochloride (L-cysteine 2HCL, 50 to 70 mg/L), L-glutamic acid (15 to 25 mg/L), 1-glutamine (450 to 460 mg/L), glycine (8 to 15 mg/L), L-histidine (10 to 20 mg/L). L-hydroxyproline (15 to 25 mg/L), L-isoleucine (45 to 55 mg/L), L-leucine (45 to 55 mg/L), L-lysine hydrochloride (L-lysine HCL, 30 to 50 mg/L), L-methionine (10 to 20 mg/L), L-phenylalanine (10 to 20 mg/L), L-proline (10 to 25 mg/L), L-serine (25 to 35 mg/l), L-threonine (15 to 25 mg/L), L-tryptophan (I to 10 mg/L), L-tyrosine $2Na_2H_2O$ (25 to 35 mg/L), L-valine (15 to 25 mg/L), biotin (0.1 to 1 mg/L), D-calcium pantothenate (D-Ca pantothenate, 0.1 to 1 mg/L), choline chloride (1 to 5 mg/L), folic Acid (0.5 to 1.5 mg/L), 1-inositol (30 to 40 mg/L), niacinamide (0.5 to 1.5 mg/L), para-aminobenzoic acid (0.5 to 1.5 mg/L), pyridoxine hydrochloride (Pyridoxine HCL, 0.5 to 1.5 mg/), riboflavin (0.1 to 1 mg/L), thiamine hydrochloride (Thiamine HCL, 0.1 to 1.5 mg/L), vitamin B12 (0.001 to 0.01 mg/L), oxaloacetic acid (0.1 to 1 g/L), insulin (0.001 to 0.01 g/L), kanamycin (0.01 to 0.1 g/L), streptomycin (0.01 to 0.1 g/L), HEPES (1 to 5 g/L), sodium hydrogen carbonate ($NaHCO_3$, 1 to 5 g/L), and pyruvic acid sodium (100 to 150 mg/L).

On the 3rd to 4th day from culture, the flask under culture was taken out to visually check the cells under a microscope, followed by adding total 200 mL of lymphomedium in accordance with an increase in cell concentration, and culturing the same in a cell incubator at 37° C. and 5% $CO_2$.

(3) Lymphocyte Culture 2

On the 5th to 8th day from culture, the flask under culture was taken out and the cells adhered to the bottom were removed by tapping a lateral side of the flask with a hand. A bagpack including 750 mL of bagpack medium was prepared and 3.75 mL of FBS was added thereto until a final concentration of FBS reaches 0.5 vol. %. A syringe port of the bagpack was opened and disinfected with 70% ethanol, followed by connecting the syringe port to a 60 mL lock type syringe. After transferring the cells cultured in the flask along with the medium using the syringe, the bag and the syringe were separated. Then, closed culture was executed in a cell incubator for bag at 37° C. under 5% $CO_2$. The bagpack medium included 100 to 300 U/ml of interleukin-2.

The bagpack medium further included some components commonly used for colony proliferation and T cell proliferation, specifically, is a medium including calcium chloride ($CaCl_2$, 50 to 60 mg/L), copper sulfate-$5H_2O$ ($CuSO_4$—$H_2O$, 0.0001 to 0.001 mg/L), iron nitrate $9H_2O$ ($Fe(NO_3)_3 \cdot 9H_2O$, 0.1 to 1 mg/L), iron sulfate-$7H_2O$($FeSO_4$-$7H_2O$, 0.1 to 0.5 mg/L), potassium chloride (KCL, 140 to 160 mg/L), magnesium chloride ($MgCl_2$, 10 to 20 mg/L), magnesium sulfate ($MgSO_4$, 20 to 30 mg/L), sodium chloride (NaCl, 3000 to 4000 mg/L), sodium hydrogen phosphate ($NaH_3PO_4$, 20 to 40 mg/L), disodium hydrogen phosphate ($Na_2HPO_4$, 20 to 40 mg/L), zinc sulfate-$7H_2O$ ($ZnSO_4$-$7H_2O$, 0.1 to 1 mg/L), D-glucose (1500 to 1600 mg/L), Na hypoxanthine (1 to 5 mg/L), linoleic acid (0.01 to 0.1 mg/L), lipoic acid (0.01 to 0.1 mg/L), phenol red (1 to 10 mg/L), putrescine 2 hydrochloride (putrescine 2HCL, 0.01 to 0.1 mg/L), sodium pyruvate (50 to 60 mg/L), thymidine (0.1 to 0.5 mg/L), L-alanine (1 to 5 mg/L), L-arginine-hydrochloride (L-arginine-HCL, 70 to 80 mg/L), L-asparagine-$H_2O$ (to 5 mg/L), L-aspartic acid (1 to 5 mg/L), L-cysteine-$H_2O$ (5 to 10 mg/L). L-cysteine 2 hydrochloride (L-cysteine 2HCL, 10 to 20 mg/L), L-glutamic acid (1 to 5 mg/l), i-glutamine (280 to 290 mg/L), glycine (5 to 15 mg/L), L-histidine hydrochloride-$H_2O$ (L-histidine HCL-$H_2O$, 10 to 20 mg/L), L-isoleucine (20 to 30 mg/L), L-leucine (25 to 35 mg/L). L-lysine hydrochloride (L-Lysine HCL, 40 to 50 mg/L), L-methionine (5 to 10 mg/L), L-phenylalanine (15 to 20 mg/L), L-proline (5 to 10 mg/L), L-serine (10 to 15 mg/L), L-threonine (20 to 30 mg/L), L-tryptophan (1 to 10 mg/L), L-tyrosine $2Na_2H_2O$ (25 to 30 mg/L), L-valine (20 to 30 mg/L), biotin (0.001 to 0.01 mg/L), D-calcium pantothenate (D-Ca pantothenate, 1 to 5 mg/L), choline chloride (to 10 mg/L), folic acid (1 to 5 mg/L), 1-inositol (1 to 10 mg/L), niacinamide (1 to 5 mg/L), pyridoxine hydrochloride (pyridoxine HCL, 1 to 5 mg/L), riboflavin (0.1 to 0.5 mg/L), thiamine hydrochloride (thiamine HCL, 1 to 5 mg/L), vitamin B12 (0.1 to 0.5 mg/L), oxaloacetic acid (0.1 to 0.5 g/L), insulin (0.001 to 0.01 g/L), kanamycin (0.01 to 0.1 g/L), streptomycin (0.01 to 0.1 g/L), HEPES (1 to 5 g/L), sodium hydrogen carbonate ($NaHCO_3$, 0.1 to 1 g/L), albumin (0.1 to 1 g/L), selenium (0.001 to 0.01 g/L), and AIM-V (400 to 600 ml).

(4) Lymphocyte Culture 3

After 3 to 8 days from culture in the bag, a split bag containing 1,000 ml of split medium was prepared and 10 ml of FBS was added thereto through a syringe port until a concentration of FBS reaches 1 vol. %. Both lines of the split bag and the bagpack including the cells under culture are bonded using a sterile connection device. After putting the whole amount of split medium of the split bag into the bagpack containing the cells, the bagpack was equally divided so that the same amount of content in the bag enters each culture vessel, followed by divisionally bonding two divided bags using a sterile binder. After that, closed culture was executed in a cell incubator at 37° C. under 5% $CO_2$ for 3 days or more. The split medium included 100 to 300 U/ml of interleukin-2.

The split medium further included some components commonly used for colony proliferation and long term culture, specifically, is a medium including calcium chloride ($CaCl_2$, 100 to 120 mg/L), copper sulfate-5H2O ($CuSO_4$-5H2O, 0.001 to 0.01 mg/L), iron nitrate $9H_2O$ ($Fe(NO_3)_3 \cdot 9H_2O$, 0.01 to 0.1 mg/L), iron sulfate-$7H_2O$ ($FeSO_4$-$7H_2O$, 0.1 to 1 mg/L), potassium chloride (KCl, 300 to 320 mg/L), magnesium chloride ($MgCl_2$, 25 to 30 mg/L), magnesium sulfate ($MgSO_4$, 45 to 50 mg/L), sodium chloride (NaCl, 6500 to 7500 mg/L), sodium hydrogen phosphate ($NaH_3PO_4$, 60 to 70 mg/L), disodium hydrogen phosphate ($Na_2HPO_4$, 70 to 80 mg/L), zinc sulfate-7H2O ($ZnSO_4$-$7H_2O$, 0.1 to 1 mg/L). D-glucose (3100 to 3200 mg/L), Na hypoxanthine (1 to 5 mg/L), linoleic acid (0.01 to 0.1 mg/L), lipoic acid (0.1 to 0.5 mg/L), phenol red (5 to 10 mg/l), putrescine 2 hydrochloride (putrescine 2HCl, 0.01 to 1 mg/L), sodium pyruvate (100 to 120 mg/L), thymidine (0.1 to 1 mg/L). L-alanine (I to 10 mg/L), L-arginine-hydrochloride (L-arginine-HCL, 140 to 160 mg/L), L-asparagine-$H_2O$ (5 to 10 mg/L), L-aspartic acid (5 to 10 mg/L), L-cysteine-$H_2O$ (15 to 20 mg/L), L-cysteine 2 hydrochloride (L-cysteine 2HCL, 30 to 35 mg/L). L-glutamic acid (5 to 10 mg/L). L-glutamine (560 to 570 mg/L, glycine (15 to 20 mg/L), L-histidine hydrochloride-$H_2O$ (L-histidine HCL-$H_2O$, 30 to 35 mg/L), L-isoleucine (50 to 60 mg/L), L-leucine (55 to 65 mg/L). L-lysine hydrochloride (L-lysine HCL, 85 to 95 mg/L), L-methionine (15 to 20 mg/L). L-phenylalanine (30 to 40 mg/L), L-proline (15 to 20 mg/L), L-serine (20 to 30 mg/L), L-threonine (50 to 55 mg/L), L-tryptophan (5 to 10 mg/L), L-tyrosine $2Na2H_2O$ (50 to 60 mg/L), L-valine (50 to 55 mg/L), biotin (0.001 to 0.01 mg/L), D-calcium pantothenate (D-Ca pantothenate, 1 to 5 mg/L), choline chloride (5 to 15 mg/L), folic acid (1 to 5 mg/L), I-inositol (10 to 15 mg/L), niacinamide (1 to 5 mg/L), pyridoxine hydrochloride (pyridoxine HCL, 1 to 5 mg/L), riboflavin (0.1 to 1 mg/L), thiamine hydrochloride (thiamine HCL, 1 to 5 mg/L), vitamin B12 (0.1 to 1 mg/L), oxaloacetic acid (0.1 to 1 g/L), insulin (0.001 to 0.01 g/L), kanamycin (0.01 to 0.1 g/L), streptomycin (0.01 to 0.1 g/L), HEPES (1 to 5 g/L), sodium hydrogen carbonate ($NaHCO_3$, 1 to 5 g/L), albumin (0.5 to 1.5 g/L) and selenium (0.001 to 0.01 g/L.

(5) Confirmation of Contamination and Performance

Before collecting the cells, a test sample of the product under culture was taken to confirm contamination and performance of the product.

(5)-1: 3 days before cell collection, the culture solution was shaken to evenly mix the cells after conducting a cell visual test. Firstly, after disinfecting a syringe port of the bag under cell culture, 32 to 55 mL of cell culture solution was taken with a syringe and provided for requesting respective tests (A to C).

(5)-2: One day before or on the day of cell collection, the culture solution was shaken to evenly mix the cells after conducting a cell visual test. Firstly, after disinfecting a syringe port of the bag under cell culture, 24 to 30 mL of the cell culture solution was taken with a syringe and provided for requesting respective tests (D and E).

A: Sterility test
B: Mycoplasma negative test
C: Adventitious virus negative test
D: Confirmation test and purity test
E: Potency test (6) Cell Collection Culture was terminated on the 12th to 21st days from culture, and 1,000 mL of cell culture solution of one bag was transferred to four 250 mL test tubes. At this time, a collection line of the culture bag was sterilized with 70% ethanol and then cut with scissors.

After collecting the cells by centrifugation at a rotational speed of 2,000 rpm at room temperature for 5 minutes, the supernatant was removed and the cells were dispersed well using a vortex. For the remaining culture bag, the cell culture solution was collected into 4 identical test tubes, followed by centrifugation under the same conditions. The supernatant was removed and the cells were dispersed well.

After mixing human serum albumin and physiological saline to prepare a 0.1% human serum albumin solution, the cells in the test tube, were washed for a first time.

After collecting the cells by centrifugation at a rotational speed of 2,000 rpm at room temperature for 5 minutes, the supernatant was removed completely and the cells were dispersed using a vortex.

After washing the cells twice with 0.1% human serum albumin solution for a second time, the solution was subjected to centrifugation at a rotational speed of 2,000 rpm at room temperature to collect cells, remove the supernatant, and then disperse the cells using a vortex.

A 1% human serum albumin solution was prepared by mixing human serum albumin and physiological saline.

The collected cells were suspended in 1% human serum albumin solution, and then evenly mixed. A part of the specimen was collected and provided for requesting respective tests (A to D).

After disinfecting a line of the finished product filling bag with 70% ethanol, the line was cut and connected with a 50 mL syringe, followed by filling the finished product filling bag with the cell suspension.

The line of the finished product filling bag was sealed 3 times (0.5 cm) at 1 cm from the inlet, and then the second sealed part was cut to finally complete the activated lymphocyte.

A: Total cell number measurement test and cell viability test
  B: Sterility test
  C: Endotoxin test
  D: Mycoplasma detection test 2. Preparing Method 2

(1) Blood Collection and Separation of Lymphocytes

Production of the activated lymphocytes used in the present invention was begun by collecting 20 to 70 mL of autologous peripheral blood from a patient. The collected blood was transferred to a 250 mL test tube, diluted 3 times with RPMI1640 in a ratio of 1:2, and 30 to 40 mL of diluted blood was dispensed into a 50 mL test tube including Ficoll-paque dispensed therein, while not mixing the layers, followed by centrifugation at a rotational speed of 2,000 rpm at room temperature for 20 minutes.

After removing the upper plasma layer slowly so that the cells of the lymphocyte layer do not get sucked in, the separated monocyte layer was transferred to a 50 mL test tube. The separated monocyte layer was diluted 3 times with RPMI1640 in a ratio of 1:2, centrifuged at a rotational speed of 2.000 rpm at room temperature for 5 minutes, and then the supernatant was removed and the collected cells were dispersed.

(2) Lymphocyte Culture

The lymphocytes isolated in the above (1) were dispersed into 50 mL of lymphomedium, and dispensed into a flask coated with anti-CD3 antibody on the bottom area of 225 $cm^2$, followed by initiating culture in a cell incubator at 37° C. under 5% $CO_2$. At this time, interleukin-2 of 500 to 800 U/ml and 10% of FBS are contained in the lymphomedium.

On the 3rd to 4th day from culture, the flask under culture was taken out to visually check the cells under a microscope, total 130 mL of lymphomedium was added thereto in accordance with an increase in cell concentration, followed by culture in a cell incubator at 37° C. under 5% $CO_2$ (3) Lymphocyte Freezing On the 5th day from culture, the flask under culture was taken out to visually check the cells under a microscope in order to determine whether the cells are suitable. If the cells are suitable through visual test, the cells adhered to the bottom were removed by tapping a lateral side of the flask with a hand. At this time, it should be careful not to bubble, 500 μL of the detached cells was collected, the number of cells was counted, followed by calculating the number of cells to reach 3×10 cells or more per one freezing tube to determine how many freezing tubes are needed. Thereafter, the required freezing tubes were prepared.

FBS was added to reach 10% concentration, thereby preparing a cell freezing solution corresponding to the number of the freezing tubes.

The cultured lymphocytes in the flask were transferred to a 250 mL test tube, centrifuged at a rotational speed of 1.200 rpm at room temperature for 5 minutes, followed by clearly removing the supernatant through suction. At this time, it should be careful not to include cells in the supernatant. After tapping the cells free of the supernatant with a hand and dispersing the same by a vortex, the cells were mixed with a cell cryopreservation solution while setting an amount of the solution so that 1.8 mL of the solution was dispensed per freezing tube. A cell suspension was dispensed into the prepared freezing tube. The dispensed freezing tube was placed in a freezing container and stored in a deep freezer. After storage in the deep freezer, results of the intermediate judgment for bacteria detection test were confirmed. If the results are suitable, the freezing tube was transferred to a −196° C. nitrogen tank and stored until thawed.

(4) Stability Test of Frozen Lymphocyte 2 days after transferring the frozen lymphocytes to the −196° C. nitrogen tank, one frozen lymphocyte was taken out and put in a freezing container, followed by moving the container to a 37° C. dry bath and heating the same to melt the lymphocyte. After suspending 0.45 mL (4-fold dilution) of the frozen lymphocytes dissolved in 10 mL of a washing solution previously dispensed in a 15 mL test tube, centrifugation was conducted at a rotational speed of 1,200 rpm at room temperature for 3 minutes. After removing the supernatant of the separated cells, the cells were dispersed and suspended in 10 mL of culture medium. After collecting the sample and transferring the same to a 15 mL test tube, tests A to C were requested to the quality control team. 2 mL per well of the remaining cell suspension was dispensed into a 24 well plate and cultured in a cell incubator for flask at 37° C. under 5% $CO_2$ for 2 days. After 2 days, cells under culture in a 24 well plate were observed under a microscope to conduct a cell visual test. After collecting the cells in a 24 well plate into a 15 mL test tube, 10 μl of a test sample was collected during the process, and then the number of cells and viability were measured to determine whether they were suitable for test. By confirming results of quality tests A to C in stability experiments of frozen lymphocytes, the suitability for completion of freezing storage was determined.

A: Bacteria detection test
  B: Endotoxin test
  C: Mycoplasma detection test

3. Preparing Method 2
(1) Thawing and Culture of Lymphocyte

One frozen lymphocyte was taken out, put into a freezing container and transferred to a 37° C. dry-bath, followed by melting the same. Cells dissolved in 10 mL of a washing solution (RPMI1640 medium+1.0N HCL 3 mL) previously dispensed into a test tube were suspended and centrifuged at a rotational speed of 1,200 rpm at room temperature for 3 minutes. After removing the supernatant of the separated cells, the cells were dispersed and the cells were suspended in 40 mL of lymphomedium. During the process, 10 µl of the test sample was collected, the number of cells and the viability were measured, and 2 mL per well of the cell suspension was dispensed into a 24 well plate and cultured in a cell incubator for flask at 37° C. under 5% $CO_2$.

In the case of interleukin-2, the concentration was maintained at 100 to 800 U/ml until the end of the culture.

(2) Lymphocyte Culture 1

On the 2nd day from culture, the cells under culture in a 24 well plate were visually checked and transferred to a T225 flask. Then, 50 mL of lymphomedium was added and cultured in a cell incubator for flask at 37° C. under 5% $CO_2$. On the 4th day from culture, after visually checking the cells through a microscope, the cells under culture were dispersed, transferred to a flask coated with an anti-CD3 antibody on the bottom area of 225 cm$^2$, followed by adding 150 mL of lymphhomedium thereto. Then, culture was conducted in a cell incubator for flask at 37° C. under 5% $CO_2$.

(3) Lymphocyte Culture 2

On the 6th to 8th days from culture, the flask under culture was taken out to visually check cells under a microscope in order to determine whether the cells are suitable for test. Thereafter, the cells adhered to the bottom were removed by tapping a lateral side of the flask with a hand. 500 µL of the sample was collected and transferred to a 15 mL test tube to count the number of cells and measure viability (survival) of cells. FBS was put in the flask from which the cells were removed, until a final concentration of bagpack medium reaches 0.5%. Then, after opening a syringe port of a culture bag and disinfecting the same with 70% ethanol, a 60 mL lock type syringe was connected to the syringe port. After transferring the cultured cells to the flask along with a medium using the syringe, the syringe was separated from the bag. Closed culture was conducted in a cell incubator for bag at 37° C. under 5% $CO_2$.

(4) Lymphocyte Culture 3

After 3 to 8 days from culture in the bag, a culture bag containing 1.000 ml of split medium was prepared and FBS was added thereto through a syringe port until FBS concentration reaches 1%. Both lines of the culture bag and the bag including the cells under culture were bonded using a sterile connection device. After putting the whole amount of the split medium of the culture bag into the bag including the cells under culture, the cells were evenly divided so that the same amount of content in the bag enters each culture vessel, followed by divisionally bonding two divided bags using a sterile binder. Thereafter, closed culture was conducted in a cell incubator at 37° C. under 5% $CO_2$ for 3 days.

(5) Confirmation of Contamination and Performance

Before collecting the cells, a test sample of the product under culture was taken to confirm contamination and performance of the product.

(5)-1: 3 days before cell collection, after conducting a cell visual test, the culture solution was shaken to evenly mix the cells before collection. A syringe port of the bag under cell culture was disinfected, and then 32 to 55 mL of the cell culture solution was taken using a syringe and provided for requesting respective tests (A to C).

(5)-2: One day before or on the day of cell collection, after conducting a cell visual test, the culture solution was shaken to evenly mix the cells before collection. A syringe port of the bag under cell culture was disinfected, and then 24 to 30 mL of the cell culture solution was taken using a syringe and provided for requesting respective tests (D and 1).

A: Sterility test
B: Mycoplasma negative test
C: Adventitious virus negative test
D: Confirmation test and purity test
E: Potency test (6) Cell Collection Culture was terminated on the 12th to 21st days from culture, and 1,000 mL of cell culture solution in one bag was transferred to four 250 mL test tubes. At this time, a collection line of the culture bag was sterilized with 70% ethanol and then cut with scissors.

After collecting the cells by centrifugation at a rotational speed of 2,000 rpm at room temperature for 5 minutes, the supernatant was removed and the cells were dispersed well using a vortex. For the remaining culture bags, the cell culture solution was collected in 4 identical test tubes, followed by centrifugation under the same conditions as described above and removing the supernatant while dispersing the cells well.

After preparing a 0.1% human serum albumin solution by mixing human serum albumin and physiological saline, the cells in the test tube were washed with this solution for a first time.

After collecting the cells by centrifugation at a rotational speed of 2,000 rpm at room temperature for 5 minutes, the supernatant was removed completely and the cells were dispersed using a vortex After washing the cells with 0.1% human serum albumin solution for a second time, cells were collected by centrifugation at a rotational speed of 2,000 rpm at room temperature, followed by clearly removing the supernatant and dispersing the cells using vortex.

A 1% human serum albumin solution was prepared by mixing human serum albumin and physiological saline The collected cells were suspended in 1% human serum albumin solution, and then evenly mixed. A part of the sample was collected and provided for requesting respective tests (A to D).

After disinfecting a line of the finished product filling bag with 70% ethanol, the line was cut and connected to a 50 mL syringe, and then the finished product filling bag was filled with the cell suspension. The line of the finished product filling bag was sealed 3 times (0.5 cm) at 1 cm from the inlet, and then the second sealed part was cut to finally complete activated lymphocyte.

A: Total cell number measurement test and cell viability test
B: Sterility test
C: Endotoxin test
D: Mycoplasma detection test Cell Phenotypic Analysis of the Prepared Activated Lymphocytes In order to confirm a degree of distribution of cytokine-induced killer cells, some samples of the cultured cells were collected and analyzed by fluorescence-activated cell sorting (FACS).

IgG1-FITC, IgG1-PE and IgG1-APC were prepared as negative control antibodies, while anti-CD3-FITC, anti-CD8-PE, anti-CD8-FITC, anti-CD56-PE, anti-CD56 APC and anti-NKG2D-PE were prepared as experimental group antibodies (the same antibody with different fluorescence was used to prevent overlapping of fluorescence during double staining and triple staining). The buffer solution was used as a phosphate buffer solution containing 0.5% albumin.

The number of cells in the cultured anticancer immunocytotherapeutic agent was counted, followed by preparing the agent to have cells in an amount of $0.5 \times 10^7$ cells/mL. After centrifugation at a rotational speed of 1,600 rpm at room temperature for 4 minutes, the supernatant was removed and the buffer solution was added to reach $0.5 \times 10^7$ cells/mL. After preparing a 5 mL test tube, 100 μL of each cell suspension having $0.5 \times 10^7$ cells/mL was added thereto, in addition, the control antibody and the experimental group antibody were further added. After mixing well, the solution was subjected to reaction at room temperature for 30 minutes in a dark state. After 30 minutes, 1 mL of the buffer solution was added, followed by centrifugation at a rotational speed of 1.600 rpm at room temperature for 4 minutes. After removing the supernatant, 500 μl of the buffer solution was added, the cell phenotype was analyzed with a flow cytometer.

Anticancer Efficacy Evaluation Items and Evaluation Method of the Prepared Activated Lymphocytes, and Preparation of Animal Models for Cancer Types 1. Identification of Anti-Cancer Effects on Human Renal Cancer (ACHN)

Animal Model Preparation and Test Substance Administration

Nude mice were purchased and stored in a specific pathogen free (SPF) room of the Korea Research Institute of Bioscience and Biotechnology, and allowed to acclimate for 1 week before use. Human renal cancer, that is, ACHN cells were injected subcutaneously into each nude mouse at a concentration of $1.2 \times 10^7$ cells. From the day after cancer cell transplantation, the composition of the present invention was injected into the tail vein of the nude mouse once a week for total 4 times. As a positive control group, adriamycin was administered intravenously at a concentration of 2 mg/kg once a week for total 4 times.

In order to observe effects on tumor growth, tumor size, weight and general symptoms were observed to evaluate anticancer efficacy, and the animal's body weight was measured to verify toxicity to animals.

Statistics

Standard deviations (SDs) and p-values of all test results were calculated using ANOVA (Prisim. GraphPad software, USA) and student's t-test.

2. Identification of Anticancer Effects on Human Pancreatic Cancer (AsPC-1)

Animal Model Preparation and Test Substance Administration

Nude mice were purchased and stored in a specific pathogen free (SPF) room of the Korea Research Institute of Bioscience and Biotechnology, and allowed to acclimate for 1 week before use. Human pancreatic cancer, that is, AsPC1 cells were injected subcutaneously into each nude mouse at a concentration of $9 \times 10^6$ cells. From the day after cancer cell transplantation, the composition of the present invention was injected into the tail vein of the nude mouse once a week for total 4 times. As a positive control group, adriamycin was administered intravenously at a concentration of 2 mg/kg once a week for total 4 times.

In order to observe effects on tumor growth, tumor size, weight and general symptoms were observed to evaluate anticancer efficacy, and the animal's body weight was measured to verify toxicity to animals.

Statistics

Standard deviations (SDs) and p-values of all test results were calculated using ANOVA (Prisim, GraphPad software, USA) and student's t-test.

3. Identification of Anti-Cancer Effects on Human Melanoma Cancer (LOX-IMV1)

Animal Model Preparation and Test Substance Administration

Nude mice were purchased and stored in a specific pathogen free (SPF) room of the Korea Research Institute of Bioscience and Biotechnology, and allowed to acclimate for 1 week before use. Human melanoma cancer, that is, LOX-IMV1 cells were injected subcutaneously into each nude mouse at a concentration of $1.5 \times 10^6$ cells. From the day after cancer cell transplantation, the composition of the present invention was injected into the tail vein of the nude mouse once a week for total 3 times. As a positive control group, adriamycin was administered intravenously at a concentration of 2 mg/kg once a week for total 3 times.

In order to observe effects on tumor growth, tumor size, weight and general symptoms were observed to evaluate anticancer efficacy, and the animal's body weight was measured to verify toxicity to animals.

Statistics

Standard deviations (SDs) and p-values of all test results were calculated using ANOVA (Prisim, GraphPad software, USA) and student's t-test.

4. Identification of Anticancer Effects on Human Prostate Cancer (PC-3)

Animal Model Preparation and Test Substance Administration

Nude mice were purchased and stored in a specific pathogen free (SPF) room of the Korea Research Institute of Bioscience and Biotechnology, and allowed to acclimate for 1 week before use. Human prostate cancer, that is, PC-3 cells were injected subcutaneously into each nude mouse at a concentration of $9 \times 10^6$ cells. From the day after cancer cell transplantation, the composition of the present invention was injected into the tail vein of the nude mouse once a week for total 4 times. As a positive control group, adriamycin was administered intravenously at a concentration of 2 mg/kg once a week for total 4 times.

In order to observe effects on tumor growth, tumor size, weight and general symptoms were observed to evaluate anticancer efficacy, and the animal's body weight was measured to verify toxicity to animals.

Statistics

Standard deviations (SDs) and p-values of all test results were calculated using ANOVA (Prisim, GraphPad software, USA) and student's t-test.

5. Identification of Anticancer Effects on Human Colon Cancer (SW620)

Animal Model Preparation and Test Substance Administration

Nude mice were purchased and stored in a specific pathogen free (SPF) room of the Korea Research Institute of Bioscience and Biotechnology, and allowed to acclimate for 1 week before use. Human colon cancer, that is, SW620 cells were injected subcutaneously into each nude mouse at a concentration of $6 \times 10^6$ cells. From the day after cancer cell transplantation, the composition of the present invention was injected into the tail vein of the nude mouse once a week for total 4 times. As a positive control group, adriamycin was administered intravenously at a concentration of 2 mg/kg once a week for total 4 times.

In order to observe effects on tumor growth, tumor size, weight and general symptoms were observed to evaluate anticancer efficacy, and the animal's body weight was measured to verify toxicity to animals.

Statistics

Standard deviations (SDs) and p-values of all test results were calculated using ANOVA (Prisim, GraphPad software, USA) and student's t-test.

Cell Phenotype Analysis Results of Activated Lymphocytes

1) As a result of analyzing the cell phenotype of cytokine-induced killer cells prepared according to the above examples, $CD56^+$ cells showing the strongest cytotoxicity among various subpopulations accounted for 46.9% of the total cells. Among them, the cytokine-induced killer cells, a $CD3^+$ $CD56^+$ cell group including the cytokine-induced killer cells, which is MHC-independent and has a higher proliferation rate and cytotoxic activity than the cell group expressing $CD56^+$ alone, accounted for 44.4%, in turn accounting for 94.7% of $CD56^+$ cells. The cell group co-expressing $CD8^+$ $CD56^+$ was measured to be 32.5%. Cytotoxicity T lymphocytes co-expressing $CD3^+$ $D8^+$ were measured to be 65% (see FIG. 1).

2) As a result of analyzing expression of $CD8^+CD56^+$ by gating the activated lymphocytes prepared in the above examples with CD8+, cells expressing $CD8^+CD56^+$ $NKG2D^+$ simultaneously accounted for 28% of all the cells.

Results of Anticancer Effect Evaluation of the Prepared Activated Lymphocytes

1. Results of Evaluation of Anticancer Effects on Human Renal Cancer (ACHN)

1) Change in Tumor Size

In the case of the control group, cells were grown to a size of $321\pm47$ mm$^3$ on the 28th day, and when administering the composition of the present invention at $1\times10^6$ cells/mouse, the size was $274\pm51$ mm$^3$ to indicate 14% growth inhibition. On the other hand, when administering the composition of the present invention at $3\times10^6$ cells/mouse, the size was $209\pm26$ mm$^3$ to indicate 34% growth inhibition ($p<0.05$). Further, when administering the composition of the present invention at $10\times10^6$ cells/mouse, the size was $138\pm32$ mm$^3$ to indicate 56% growth inhibition ($p<0.01$). In the adriamycin-administered group used as a positive control group, the size was $192\pm44$ mm$^3$ to indicate 40% cancer growth inhibition.

2) Change in Tumor Weight

After the tumor was isolated on the last day (day 28), the weight was measured. In the case of the control group, the average tumor weight was $651\pm164$ mg, and when administering the composition of the present invention at $1\times10^6$ cells/mouse, the tumor weight was $530\pm100$ mg to indicate 18% growth inhibition. On the other hand, when administering the composition at $3\times10^6$ cells/mouse, the tumor weight was $435\pm118$ mg to indicate 33% growth inhibition ($p<0.05$). Further, when administering the composition of the present invention at $10\times10^6$ cells/mouse, the tumor weight was $308\pm95$ mg to indicate 52% growth inhibition ($p<0.01$). In the adriamycin-administered group used as a positive control group, the tumor weight was $409\pm41$ mg to indicate 37% cancer growth inhibition ($p<0.05$).

3) Change in Body Weight

Compared with the body weight of Day-1 (100%), on day 28, the control group showed a body weight change of 105%, while the administration group of the inventive composition showed a body weight change of 104 to 106%. Further, the adriamycin-administered group showed a normal body weight change of 95%. In addition, no abnormal behavior was observed.

4) Observation of General Symptoms

During 28 days of administering the composition of the present invention, no dead animals were observed, and no animals with abnormal behavior were observed.

2. Identification of Anticancer Effects on Human Pancreatic Cancer (AsPC-1)

1) Change in Tumor Size

In the case of the control group, the tumor was grown to $251\pm50$ mm$^3$ on the 25th day, and when administering the composition of the present invention at $1\times10^6$ cells/mouse, the size was $192\pm25$ mm$^3$ to indicate 23% growth inhibition ($p<0.05$). On the other hand, when administering the composition of the present invention at $3\times10^6$ cells/mouse, the size was $146\pm26$ mm$^3$ to indicate 42% growth inhibition ($p<0.01$). Further, when administering the composition of the present invention at $10\times10^6$ cells/mouse, the size was $73\pm30$ mm$^3$ to indicate 70% growth inhibition ($p<0.01$). In the adriamycin-administered group used as a positive control group, the size was $130\pm28$ mm$^3$ to indicate 48% cancer growth inhibition.

2) Change in Tumor Weight

After the tumor was isolated on the last day (day 25), the weight was measured. In the case of the control group, the average tumor weight was $790\pm193$ mg, and when administering the composition of the present invention at $1\times10^6$ cells/mouse, the tumor weight was $591\pm106$ mg to indicate 25% growth inhibition ($p<0.05$). On the other hand, when administering the composition at $3\times10^6$ cells/mouse, the tumor weight was $457\pm45$ mg to indicate 42% growth inhibition ($p<0.05$). Further, when administering the composition of the present invention at $10\times10^6$ cells/mouse, the tumor weight was $267\pm84$ mg to indicate 66% growth inhibition ($p<0.01$). In the adriamycin-administered group used as a positive control group, the tumor weight was $473\pm64$ mg to indicate 44% cancer growth inhibition ($p<0.01$).

3) Change in Body Weight

Compared with the body weight of Day-1 (100%), on day 25, the control group showed a body weight change of 130%, while the administration group of the inventive composition showed a body weight change of 120 to 125%. Further, the adriamycin-administered group showed a normal body weight change of 125%. In addition, no abnormal behavior was observed.

4) Observation of General Symptoms

During 25 days of administering the composition of the present invention, no dead animals were observed, and no animals with abnormal behavior were observed.

3. Identification of Anticancer Effects on Human Melanoma Cancer (LOX-IMV1)

1) Change in Tumor Size

In the case of the control group, the tumor was grown to $254\pm43$ mm$^3$ on the 15th day, and when administering the composition of the present invention at $1\times10^6$ cells/mouse, the size was $167\pm78$ mm$^3$ to indicate 34% growth inhibition ($p<0.05$). On the other hand, when administering the composition of the present invention at $3\times10^6$ cells/mouse, the size was $108\pm35$ mm$^3$ to indicate 35% growth inhibition ($p<0.01$). Further, when administering the composition of the present invention at $10\times10^6$ cells/mouse, the size was $60\pm21$ mm$^3$ to indicate 76% growth inhibition ($p<0.01$). In the adriamycin-administered group used as a positive control group, the size was $71\pm458$ mm$^3$ to indicate 72% cancer growth inhibition 2) Change in Tumor Weight After the tumor was isolated on the last day (day 15), the weight was measured. In the case of the control group, the average tumor weight was 1676±530 mg, and when administering the composition of the present invention at 1×10⁶ cells/mouse, the tumor weight was 1158±631 mg to indicate 30% growth inhibition (p<0.05). On the other hand, when administering the composition at 3×10⁶ cells/mouse, the tumor weight was 799±258 mg to indicate 52% growth inhibition (p<0.01). Further, when administering the composition of the present invention at 10×10⁶ cells/mouse, the tumor weight was 401±166 mg to indicate 76% growth inhibition (p<0.01). In the adriamycin-administered group used as a positive control group, the tumor weight was 496±306 mg to indicate 70% cancer growth inhibition (p<0.01).

3) Change in Body Weight

Compared with the body weight of Day-1 (100/o), on day 15, the control group showed a body weight change of 130%, while the administration group of the inventive composition showed a body weight change of 121 to 126%. Further, the adriamycin-administered group showed a normal body weight change of 122%. In addition, no abnormal behavior was observed.

4) Observation of General Symptoms

During 15 days of administering the composition of the present invention, no dead animals were observed, and no animals with abnormal behavior were observed.

4. Identification of Anticancer Effects on Human Prostate Cancer (PC-3)

1) Change in Tumor Size

In the case of the control group, the tumor was grown to 378±23 mm³ on the 22nd day, and when administering the composition of the present invention at 1×10⁶ cells/mouse, the size was 300±54 mm³ to indicate 20% growth inhibition (p<0.01). On the other hand, when administering the composition of the present invention at 3×10⁶ cells/mouse, the size was 211±33 mm³ to indicate 44% growth inhibition (p<0.01). Further, when administering the composition of the present invention at 10×10⁶ cells/mouse, the size was 183±22 mm³ to indicate 51% growth inhibition (p<0.01). In the adriamycin-administered group used as a positive control group, the size was 225±59 mm³ to indicate 40% cancer growth inhibition 2) Change in Tumor Weight After the tumor was isolated on the last day (day 22), the weight was measured. In the case of the control group, the average tumor weight was 1346±159 mg, and when administering the composition of the present invention at 1×10⁶ cells/mouse, the tumor weight was 1018±127 mg to indicate 24% growth inhibition (p<0.01). On the other hand, when administering the composition at 3×10⁶ cells/mouse, the tumor weight was 761±131 mg to indicate 43% growth inhibition (p<0.01). Further, when administering the composition of the present invention at 10×10⁶ cells/mouse, the tumor weight was 677±56 mg to indicate 49% growth inhibition (p<0.01). In the adriamycin-administered group used as a positive control group, the tumor weight was 808±156 mg to indicate 40% cancer growth inhibition (p<0.01).

3) Change in Body Weight

Compared with the body weight of Day-1 (100%), on day 22, the control group showed a body weight change of 103%, while the administration group of the inventive composition showed a body weight change of 103 to 106%. Further, the adriamycin-administered group showed a normal body weight change of 102%. In addition, no abnormal behavior was observed.

4) Observation of General Symptoms

During 22 days of administering the composition of the present invention, no dead animals were observed, and no animals with abnormal behavior were observed.

5. Identification of Anticancer Effects on Human Colon Cancer (SW620)

1) Change in Tumor Size

In the case of the control group, the tumor was grown to 473±190 mm³ on the 25th day, and when administering the composition of the present invention at 1×10⁶ cells/mouse, the size was 436±214 mm³ to indicate 7% growth inhibition (not significant). On the other hand, when administering the composition of the present invention at 3×10⁶ cells/mouse, the size was 220±138 mm³ to indicate 53% growth inhibition (p<0.05). Further, when administering the composition of the present invention at 10×10⁶ cells/mouse, the size was 127±60 mm³ to indicate 73% growth inhibition (p<0.01). In the adriamycin-administered group used as a positive control group, the size was 142±97 mm³ to indicate 48% cancer growth inhibition (p<0.05).

2) Change in Tumor Weight

After the tumor was isolated on the last day (day 25), the weight was measured. In the case of the control group, the average tumor weight was 1661±817 mg, and when administering the composition of the present invention at 1×10⁶ cells/mouse, the tumor weight was 1482±659 mg to indicate 10% growth inhibition (not significant). On the other hand, when administering the composition at 3×10⁶ cells/mouse, the tumor weight was 765±424 mg to indicate 53% growth inhibition (p<0.05). Further, when administering the composition of the present invention at 10×10⁶ cells/mouse, the tumor weight was 440±222 mg to indicate 73% growth inhibition (p<0.001). In the adriamycin-administered group used as a positive control group, the tumor weight was 834±306 mg to indicate 49% cancer growth inhibition (p<0.05).

3) Change in Body Weight

Compared with the body weight of Day-1 (100%), on day 25, the control group showed a body weight change of 116%, while the administration group of the inventive composition showed a body weight change of 120 to 121%. Further, the adriamycin-administered group showed a normal body weight change of 114%. In addition, no abnormal behavior was observed.

4) Observation of General Symptoms

During 25 days of administering the composition of the present invention, no dead animals were observed, and no animals with abnormal behavior were observed.

TABLE 1

| Cell line | Organ | Cell No.[a] | Days[b] | Control[c] | CIK(1)[d] | CIK(3)[e] | CIK(10)[f] | ADR[g] |
|---|---|---|---|---|---|---|---|---|
| ACHN | Renal | 1.2 × 10⁷ | 28 | 100 ± 25 | 81 ± 15 | 67 ± 18 | 47 ± 15 | 63 ± 6 |
| AsPC-1 | Pancreas | 9 × 10⁶ | 25 | 100 ± 24 | 75 ± 13 | 58 ± 6 | 34 ± 11 | 55 ± 8 |
| LOX-IMVI | Skin | 1.5 × 10⁶ | 15 | 100 ± 32 | 69 ± 38 | 48 ± 15 | 24 ± 10 | 30 ± 18 |

TABLE 1-continued

| Cell line | Organ | Cell No.[a] | Days[b] | Control[c] | CIK(1)[d] | CIK(3)[e] | CIK(10)[f] | ADR[g] |
|---|---|---|---|---|---|---|---|---|
| PC-3 | Prostate | $9 \times 10^6$ | 22 | 100 ± 12 | 76 ± 9 | 57 ± 10 | 50 ± 4 | 60 ± 12 |
| SW-620 | Colon | $6 \times 10^6$ | 25 | 100 ± 53 | 89 ± 48 | 55 ± 39 | 31 ± 12 | 54 ± 28 |

[a]Number of human cancer cells administered to nude mouse
[b]Last day of tumor weight measurement and experiment
[c]Tumor growth rate of the control group (%)
[d]Tumor growth rate (%) of the group administered the anticancer immunocytotherapeutic agent composition ($1 \times 10^6$ cells/mouse) compared to the control group
[e]Tumor growth rate (%) of the group administered the anticancer immunocytotherapeutic agent composition ($3 \times 10^6$ cells/mouse) compared to the control group
[f]Tumor growth rate (%) of the group administered the anticancer immunocytotherapeutic agent composition ($1 \times 10^6$ cells/mouse) compared to the control group
[g]Tumor growth rate (%) of the group administered with adriamycin (2 mg/kg) compared to the control group Domestic Clinical Trial of Activated Lymphocytes 1. Liver Cancer Clinical Trial According to the liver cancer AJCC stage classification method (6th edition), the safety and effectiveness of the composition of the present invention were evaluated in 230 patients who received curative treatment (surgical resection, radiofrequency heat therapy, or percutaneous ethanol infusion) in the first or second stage of hepatocellular carcinoma. The median of recurrence free survival (RFS) was 44 months in the immunotherapy group and 30 months in the control group (p=0.010), thereby demonstrating a statistically significant difference of HR 0.63 (95% CI, 0.43-0.94). As a secondary outcome variable, the overall survival rate was longer in the immunotherapy group with HR 0.21 (95% CI, 0.06-0.75; p=0.008) compared to the control group.

2. Long-Term Follow-Up of Liver Cancer Clinical Trials

Among the patients who participated in the clinical trial, those who agreed to the long-term follow-up by signing were followed up for long-term survival rates of recurrence up to 36 months at an interval of up to 6 months from the date of the end of the clinical trial. The survival rate without recurrence at 60 months was 44.8% in the immunotherapy group and 33.1% in the control group, thereby demonstrating a statistically significant difference (p=0.0033).

3. Glioblastoma Clinical Trial

The effectiveness of the composition of the present invention was evaluated for patients with glioblastoma. The median of progression free survival (PFS) was 8.1 months in the immunotherapy group (95% confidence interval (CI), 5.8 to 8.5 months) and 5.4 months in the control group (95% CI, 3.3 to 7.9 months, p=0.0401). The median of overall survival period was 22.5 months (95% CI, 17.2 to 23.9 months) in the immunotherapy group and 16.9 months (95% CI, 13.9 to 21.9 months) in the control group, and there was no statistically significant difference. However, it was prolonged by 5.6 months in the immunotherapy group.

4. Pancreatic Cancer Clinical Trial

The effectiveness of the composition of the present invention was evaluated for patients with pancreatic cancer. The median of survival without disease progression was 11.0 weeks (95% CI 8.8 to 13.2 weeks), and the median of overall survival was 26.6 weeks (95% CI 8.6 to 44.6 weeks). The 6 month survival rate from the date of registration was 60%.

The invention claimed is:

1. A method for preparation of activated lymphocytes comprising CD8$^+$CD56$^+$NKG2D$^+$ cells, the method comprising culturing lymphocytes isolated from peripheral blood in a medium in three steps,
   wherein a medium in a first step contains an anti-CD3 antibody, interleukin-2 and fetal bovine serum (FBS), a medium in a second step and a third step contains interleukin-2 and FBS and does not contain the anti-CD3 antibody, and
   wherein a concentration of the anti-CD3 antibody is from 1 to 10 µg/ml, a concentration of interleukin-2 in each of the first, the second and the third step is from 100 to 800 U/ml, and a concentration of FBS in the first step is from 5 to 15% by volume, a concentration of FBS in the second step is from 0.1 to 1% by volume, and a concentration of FBS in the third step is from 0.1 to 2% by volume.

* * * * *